(12) United States Patent
Ritscher et al.

(10) Patent No.: US 7,031,765 B2
(45) Date of Patent: Apr. 18, 2006

(54) ALGORITHMS FOR DETECTING ATRIAL ARRHYTHMIAS FROM DISCRIMINATORY SIGNATURES OF VENTRICULAR CYCLE LENGTHS

(75) Inventors: David E. Ritscher, Minneapolis, MN (US); Shantanu Sarkar, St. Paul, MN (US)

(73) Assignee: Medtronic, Inc, Minneapolis, MN (US)

( * ) Notice: Subject to any disclaimer, the term of this patent is extended or adjusted under 35 U.S.C. 154(b) by 521 days.

(21) Appl. No.: 10/292,285

(22) Filed: Nov. 11, 2002

(65) Prior Publication Data

US 2004/0092836 A1 May 13, 2004

(51) Int. Cl.
*A61B 5/046* (2006.01)
(52) U.S. Cl. .................................................. 600/518
(58) Field of Classification Search ................ 600/508, 600/510, 515, 516, 518
See application file for complete search history.

(56) References Cited

U.S. PATENT DOCUMENTS

| | | | |
|---|---|---|---|
| 4,947,858 A | 8/1990 | Smith | |
| 5,285,793 A | 2/1994 | Slovut et al. | |
| 5,312,446 A | 5/1994 | Holschbach et al. | |
| 5,622,178 A * | 4/1997 | Gilham | 600/523 |
| 5,682,901 A | 11/1997 | Kamen | |
| 5,984,954 A | 11/1999 | Cohen | |
| 5,987,352 A | 11/1999 | Klein et al. | |
| 6,230,059 B1 | 5/2001 | Duffin | |
| 6,308,100 B1 | 10/2001 | Er et al. | |
| 6,314,321 B1 * | 11/2001 | Morris | 607/9 |
| 6,363,281 B1 | 3/2002 | Zhu et al. | |
| 6,370,432 B1 | 4/2002 | Conley et al. | |
| 6,374,139 B1 | 4/2002 | Er et al. | |
| 6,377,851 B1 | 4/2002 | Shieh et al. | |

(Continued)

FOREIGN PATENT DOCUMENTS

DE 10248213 8/2003

(Continued)

OTHER PUBLICATIONS

Woo et al., "Patterns of Beat-to-Beat Heart Rate Variability in Advanced Heart Failure," *American Heart Journal*, vol. 123, No. 3, p. 704-710 (Mar. 1992).

(Continued)

*Primary Examiner*—Robert E. Pezzuto
*Assistant Examiner*—Kristen Mullen
(74) *Attorney, Agent, or Firm*—Daniel G. Chapik; Girma Wolde-Michael

(57) ABSTRACT

Detection of arrhythmias is facilitated using irregularity of ventricular beats measured by delta-RR (ΔRR) intervals that exhibit discriminatory signatures when plotted in a Lorenz scatter-plot. An "AF signature metric" is established characteristic of episodes of AF that exhibit highly scattered (sparse) distributions or formations of 2-D data points. An "AFL signature metric" is established characteristic of episodes of AFL that exhibit a highly concentrated (clustered) distribution or formation of 2-D data points. A set of heart beat interval data is quantified to generate highly scattered (sparse) formations as a first discrimination metric and highly concentrated (clustered) distributions or formations as a second discrimination metric. The first discrimination metric is compared to the AF signature metric, and/or the second discrimination metric is compared to the AFL signature metric. AF or HFL is declared if the first discrimination metric satisfies either one of the AF signature metric.

41 Claims, 12 Drawing Sheets

U.S. PATENT DOCUMENTS

| | | | |
|---|---|---|---|
| 6,389,308 | B1 | 5/2002 | Shusterman |
| 6,389,316 | B1 | 5/2002 | Bornzin et al. |
| 6,496,731 | B1 * | 12/2002 | Lovett .......................... 607/14 |
| 2001/0044586 | A1 | 11/2001 | Ferek-Petric |
| 2001/0051764 | A1 | 12/2001 | Bardy |
| 2002/0002390 | A1 | 1/2002 | Fischell et al. |
| 2002/0007198 | A1 | 1/2002 | Haupert et al. |
| 2002/0042636 | A1 | 4/2002 | Koshiol et al. |
| 2004/0176697 | A1 * | 9/2004 | Kappenberger et al. .... 600/518 |
| 2005/0004486 | A1 * | 1/2005 | Glass et al. ................. 600/515 |

FOREIGN PATENT DOCUMENTS

| | | |
|---|---|---|
| EP | 1 118 945 | 7/2001 |
| WO | WO 98/02209 | 1/1998 |
| WO | WO 01/56653 | 8/2001 |

OTHER PUBLICATIONS

Tateno et al., "A Method for Detection of Atrial Fibrillation Using RR Intervals," *Computers in Cardiology 2000*, vol. 27, p. 391-394 (2000).

Nakatsu et al., "Silent Zone on Lorenz Plots of the Ventricular Response Before Termination of Paroxysmal Atrial Fibrillation," *Japanese Circulation Journal*, vol. 58, p. 676-682 (Aug. 1994).

Pedich et al., "The Mechanism of the Silent Zone on Lorenz Plots in Atrial Fibrillation," *Roczniki Akademii Medycznej w Bialymstoku*, vol. 43, p. 232-244 (1998).

Nagumo et al., "Application of the Lorenz Plot to Analysis of Ventricular Arrhythmias," *AHA Meeting 1992*, Abstract P-28, p. 96 (1992).

Kim et al., "Application of the Lorenz Plot to Analysis of Autonomic Cardiovascular Functions," *AHA Meeting 1992*, Abstract P-34, p. 102 (1992).

Brochure, Oxford Medilog Excel Holter Management System, Heart Rate Variability, Oxford Medical Inc., Clearwater, FL, no date.

Anan et al., "Arrhythmia Analysis by Successive RR Plotting," *Journal of Electrocardiology*, vol. 23, No. 3, p. 243-248 (Jul. 1990).

Hnatkova et al., "Numeric Processing of Lorenz Plots of R-R Intervals From Long-term ECGs," *Journal of Electrocardiology*, vol. 28 (Supplement), p. 74-80 (1995).

Oka et al., "Double-Sector Lorenz Plot Scattering in an R-R Interval Analysis of Patients With Chronic Atrial Fibrillation," *Journal of Electrocardiology*, vol. 31, No. 3, p. 228-235 (1998).

* cited by examiner

ΔRR Lorenz Plot for a 2 min AF episode

ΔRR Lorenz Plot for a 2 min NSR episode

ΔRR Lorenz Plot for a 2 min AFl episode

ΔRR Lorenz Plot for a 2 min episode of ectopy

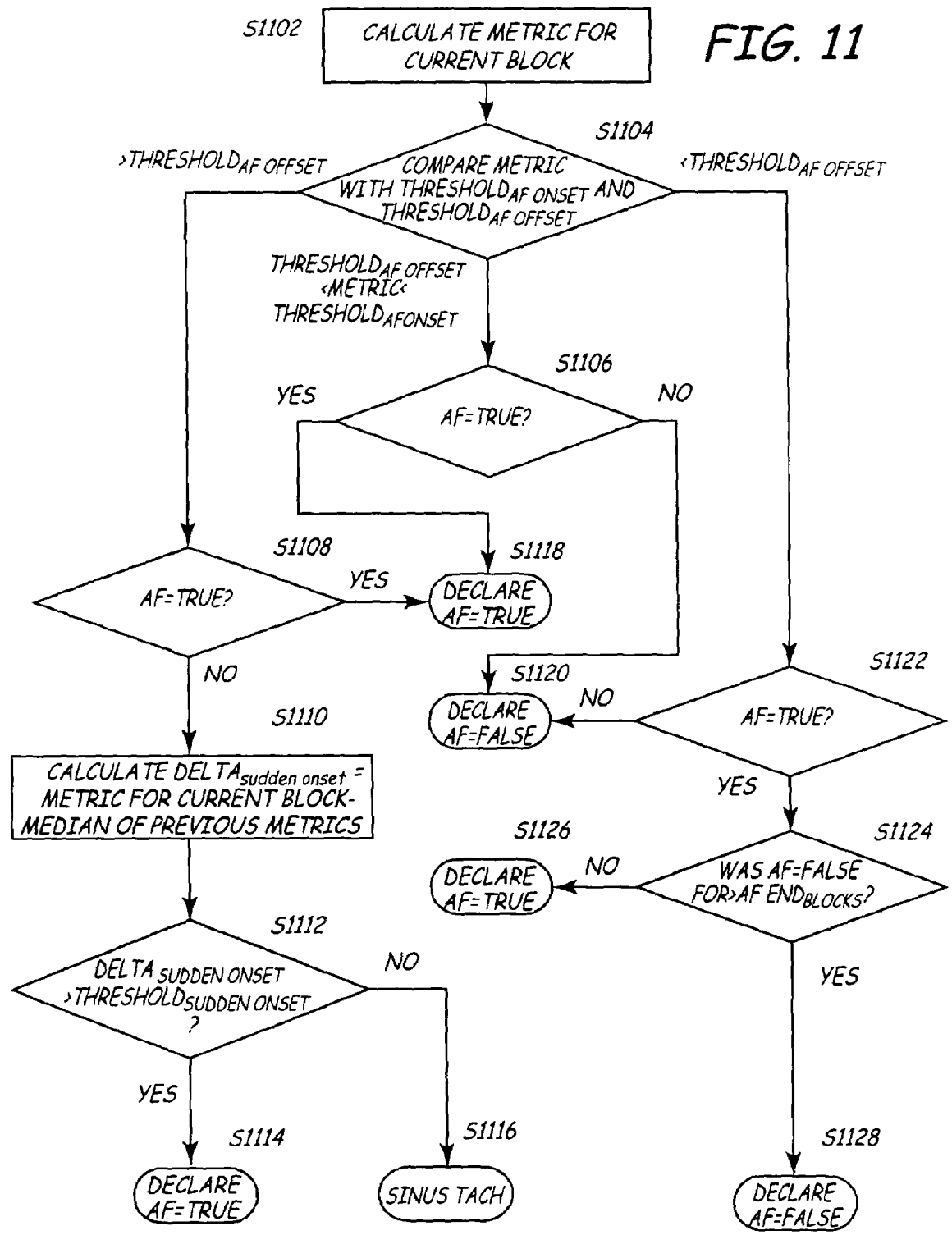

ALGORITHMS FOR DETECTING ATRIAL ARRHYTHMIAS FROM DISCRIMINATORY SIGNATURES OF VENTRICULAR CYCLE LENGTHS

The present invention relates to detection of atrial arrhythmias, particularly atrial fibrillation (AF) and atrial flutter (AFL) using discriminatory signatures of the ventricular cycle lengths.

BACKGROUND OF THE INVENTION

The mechanical events of the heart are preceded and initiated by the electrochemical activity of the heart (i.e., the propagation of the action potential). In a healthy heart, the electrical and mechanical operation of the heart is regulated by electrical signals produced by the heart's sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the "Bundle of His" of the ventricular septum and thereafter to the "Bundle Branches" and the Purkinje muscle fibers of the right and left ventricles. The signals propagated through the Bundle Branches effects depolarization and accompanying contraction of the left ventricle and the right ventricle in close order. Following contraction, the myocardial cells repolarize during a short period of time, returning to their resting state. The right and left atria refill with venous and oxygenated blood, respectively, until the cardiac cycle is again commenced by a signal originating from the SA node. At rest, the normal adult SA node produces an atrial depolarization signal approximately 60 to 85 times a minute, causing the heart muscle to contract, and thereby pumping blood to the remainder of the body. The electrical signal passes through the heart chambers as a wave front that can be characterized as a plane advancing from cell to cell through the cardiac muscle that separates cells of different electrical potential as a function of the time that it takes to complete the cardiac cycle.

The above-described cardiac cycle is disrupted in diseased or injured hearts, and the chronic or episodic disrupted electrical activity has long been employed to diagnose the state of the heart. A variety of techniques have been developed for collecting and interpreting data concerning the electrical activity of the heart using external medical devices (EMDs) both in the clinical setting and by way of portable external monitors worn by an ambulatory patient or implantable medical devices (IMDs) implanted in an ambulatory patient to collect data relating to electrical heart function during daily activities of the patient. Such techniques include electrocardiography, vectorcardiography and polarcardiography.

The cardiac cycle as displayed in an ECG lead tracing reflects the electrical wave front as measured across an ECG lead, that is between two spaced apart electrodes on the patient's body, as shown in U.S. Pat. No. 4,587,976, for example. The portion of a cardiac cycle representing atrial depolarization is referred to as a "P-wave." Depolarization of the ventricular muscle fibers is represented by "Q", "R", and "S" points of a cardiac cycle. Collectively these "QRS" points are called an "R-wave" or a "QRS complex." Repolarization of the depolarized heart cells occurs after the termination of another positive deflection following the QRS complex known as the "T-wave." The QRS complex is the most studied part of the cardiac cycle and is considered to be the most important for the prediction of health and survivability of a patient. However, the time relation of the P-wave to the QRS complex and the height and polarity of the T-wave and S-T segment are also indicators of a healthy or diseased heart. The S-T segment of a healthy heart is usually isoelectric, i.e., neither positive nor negative in deflection from baseline of the ECG lead tracing. This S-T segment is a most important indicator of the health of the ventricular myocardium and is elevated in ischemia and due to infarctions disrupting the depolarization wave front.

The beat rate of a normal heart is governed by the atrial depolarization rate, which is regulated by the body's current requirement for cardiac output reflecting a level of physical exercise or stress. The normal cardiac cycle and heart rate described above are disrupted in many instances. Conduction defects affecting the A-V node response to a P-wave can cause the ventricles to beat too slowly, that is exhibit bradycardia, and not provide sufficient cardiac output. Other conduction defects and/or disease processes can cause the atria and/or ventricles to spontaneously depolarize at a rapid rate, that is, to exhibit a tachyarrhythmia, that diminishes or disrupts cardiac output. Such ventricular tachyarrhythmias include ventricular tachycardia (VT) and ventricular fibrillation (VF).

In AF, the atria depolarize at an elevated rate that is often highly irregular, and the atrial depolarizations are typically conducted intermittently to the ventricles, so that the ventricles beat synchronously at times and asynchronously at other times with the atrial depolarizations. In AFL, the atria beat at an elevated rate that is highly regular, and a portion of the atrial depolarizations are typically conducted to the ventricles, whereby the ventricles often beat synchronously with every second or third atrial depolarization. Thus, the ventricular heart rate can be in a normal range or elevated but is often regular during an AFL episode, whereas the ventricular heart rate can be in a normal range or elevated but is usually irregular during an AF episode. Episodes of AF and AFL affect the atrial mechanical function and can have an effect on the ventricular heart rate that negatively affects cardiac output of the ventricles. These episodes can be accompanied by faintness, syncope, and tachyarrhythmia palpitation symptoms and can occur spontaneously and intermittently.

Moreover, at times, the atria prematurely contract due to depolarizations initiated at ectopic foci other than the SA Node in the atrium, referred to as Premature Atrial Contractions (PACs) or ectopic P-waves. These PACs can be conducted to the ventricles to result in a ventricular contraction or can, due to their amplitude, be mistakenly detected in the ventricles as an R-wave or a ventricular depolarization conducted from the AV node.

Similarly, the ventricles can also develop ectopic foci that intermittently cause a spontaneous depolarization wave front or Premature Ventricular Contractions (PVCs) or ectopic R-waves. Such PACs and PVCs and other arrhythmias can be visually identified by trained medical care providers in the PQRST segments displayed on ECG tracings, if they manifest in the clinical setting.

The ventricular heart rate is determined as a function of the interval between successive ventricular depolarizations each marked by the R-wave of the electrocardiogram (ECG) or electrogram (EGM), that is, the RR interval between successive detected R-waves. Generally, the time interval between successive R-waves is denoted as the RR interval, and the difference between successive RR intervals is denoted as the ΔRR interval or the dRR interval in the figures. A rapid and regular or irregular ventricular heart rate can be a normal sinus rhythm (NSR) tracking the normal atrial heart rate or can be due to PVCs and/or PACs or conducted AF or AFL or due to VT or VF originating in the ventricles.

There are many instances where it is desirable to be able to diagnose intermittent spontaneous cardiac arrhythmias, particularly AF and AFL, in ambulatory patients. There is a recognized need to improve the capability of detecting and distinguishing various types of atrial and ventricular tachyarrhythmias from NSR and one another For many years, such patients, as well as patients suffering other bradyarrhythmias and tachyarrhythmias, have been equipped with external ECG monitoring systems, e.g., the patient-worn, real time Holter monitors, that continuously sample the ECG from skin electrodes and record it over a certain time period. Then, the ECG data must be analyzed to locate evidence of an arrhythmia episode and its nature and characteristics from which a diagnosis can be made.

As described in commonly assigned U.S. Pat. No. 5,312, 446 and in U.S. Pat. No. 4,947,858, both incorporated herein by reference, the externally worn ECG recorders have inherent limitations in the memory capacity for storing sampled ECG and EGM data. Cost, size, power consumption, and the sheer volume of data over time have limited real time external Holter monitors to recording 24-hour or 48-hour segments or recording shorter segments.

The use of the externally worn Holter monitor coupled with skin electrodes is also inconvenient and uncomfortable to the patient. The skin electrodes can work loose over time and with movement by the patient, and the loose electrodes generates electrical noise that is recorded with the EGM signal and makes its subsequent analysis difficult. It has long been desired to provide an implantable monitor or recorder that is hardly noticeable by the patient and provides capabilities, such as recording ECG data correlated with an arrhythmia episode that is automatically detected or gathering statistics about a patient's clinical condition, such as the number of hours/day of arrhythmias the patient is experiencing.

Over the last 40 years, a great many IMDs have been clinically implanted in patients to treat cardiac arrhythmias and other disorders including implantable cardioverter/defibrillators (ICDs) and pacemakers having single or dual chamber pacing capabilities, cardiomyostimulators, ischemia treatment devices, and drug delivery devices. Recently developed implantable pacemakers and ICDs employ sophisticated atrial and/or ventricular tachyarrhythmia detection criteria based on heart rate, rate stability and onset and/or the morphology and other characteristics of the atrial and/or ventricular EGM. Most of these ICDs employ electrical leads bearing bipolar electrode pairs located adjacent to or in an atrial and/or ventricular heart chamber for sensing a near field EGM or having one of the electrodes located on the ICD housing for sensing a far field, unipolar EGM. In either case, the near field or far field EGM signals across the electrode pairs are filtered and amplified in sense amplifiers coupled thereto and then processed for recording the sampled EGM or for deriving atrial and/or ventricular sense event signals from P-waves and/or R-waves of the EGM.

The atrial sense event signals are typically generated by atrial sense amplifiers when the P-wave amplitude exceeds an atrial sense threshold. Similarly, the ventricular sense event signals are typically generated by ventricular sense amplifiers when the R-wave amplitude exceeds a ventricular sense threshold. The ventricular heart rate is typically derived from the measured RR interval between successive ventricular sense event signals.

In current ICDs providing a therapy for treating a cardiac arrhythmia, the sense event signals and certain aspects of the sampled EGM waveform are utilized to automatically detect a cardiac bradyarrhythmia or tachyarrhythmia in one or more heart chamber and to control the delivery of an appropriate therapy in accordance with detection and therapy delivery operating algorithms. In such cardiac ICDs providing pacing or cardioversion/defibrillation therapies, both analog and digital signal processing of the EGM is continuously carried out to sense the P-wave and/or R-wave events and to determine when a cardiac arrhythmia episode occurs. For example, a digital signal processing algorithm is employed to distinguish various atrial and ventricular tachyarrhythmias from one another. However, single chamber ICDs are more typically implanted to respond to single chamber tachyarrhythmias, and do not sense in both the atria and ventricles.

It is of great importance that such single chamber ventricular ICDs that are implanted to detect malignant ventricular tachyarrhythmia episodes, e.g. malignant VT or VF, accurately detect such VT and VF episodes to trigger delivery of the programmed ventricular anti-tachyarrhythmia therapy. An AF or AFL episode can so affect the apparent RR intervals that are being monitored as to satisfy the VT/NF detection criteria, triggering the delivery of an inappropriate and possibly dangerous VT/VF therapy. An inappropriately delivered VT/VF cardioversion/defibrillation shock therapy could induce a VT/NF episode rather than terminate the nonexistent VT/NF episode. Therefore, it is necessary to accurately discriminate between such atrial and ventricular tachyarrhythmias to avoid such occurrences.

When a tachyarrhythmia episode is detected in an ICD, at least selected EGM signal segments and sense event histogram data or the like are stored on a FIFO basis in internal RAM for telemetry out to an external programmer at a later time. Many of these ICDs are also capable of being operated to sample the EGM and transmit real time EGM data of indefinite length via uplink telemetry transmissions to the external programmer when a medical care provider initiates a real time telemetry session using the programmer.

Implantable cardiac monitors have also been developed and clinically implanted that employ the capability of recording cardiac EGM data for subsequent interrogation and uplink telemetry transmission to an external programmer for analysis by a physician. The recorded data is periodically uplink telemetry transmitted to a programmer operated by the medical care provider in an uplink telemetry transmission during a telemetry session initiated by a downlink telemetry transmission and receipt of an interrogation command.

The MEDTRONIC® Reveal™ insertable loop recorder is a form of implantable monitor that is intended to be implanted subcutaneously and has a pair of sense electrodes spaced apart on the device housing that are used to pick up the cardiac far field EGM which in this case is also characterized as a "subcutaneous ECG". The Reveal™ insertable loop recorder samples and records one or more segment (depending on the programmed operating mode) of such far-field EGM or subcutaneous ECG signals when the patient feels the effects of an arrhythmic episode and activates the recording function by applying a magnet over the site of implantation. For example, the storage of a programmable length segment of the EGM can be initiated when the patient feels faint due to a bradycardia or tachycardia or feels the palpitations that accompany certain tachycardias. The memory capacity is limited, and so the segments of such EGM episode data that are stored in memory can be written over with new EGM episode data when the patient triggers storage and the memory is full. The most recently stored segment or segments of episode data is transmitted via an uplink telemetry transmission to an external programmer when a memory interrogation telemetry session is initiated by the physician or medical care provider using the programmer. Aspects of the Reveal™ insertable loop recorder are disclosed in commonly assigned PCT publication WO98/02209 and in U.S. Pat. Nos. 5,987,352 and 6,230,059.

There are a variety of techniques known in the art for reducing raw data, e.g., recorded ECG or EGM data, to a more meaningful form. One such method is the statistical analysis to reduce the raw data to one or more statistical numbers representative of the raw data. Morphological techniques have been developed to compare sample ECG waveforms to waveform templates representative of NSR, and various arrhythmia templates. Various ways of categorizing heart rate in 1-D histograms, including the morphology of RR intervals collected from patients during known NSR and AF episodes have also been investigated in the effort to automate the detection of AF.

In, "A Method for Detection of Atrial Fibrillation Using RR Intervals", by Tateno et al., published in *Computers in Cardiology* 2000, 27:391–394, the authors describe a method for automatic detection of atrial fibrillation (AF) based on comparison of density histograms of a number, e.g., 100, successive RR intervals and ΔRR intervals from a patient recording to a plurality of standard density histograms of a like number of either successive RR intervals or ΔRR intervals derived from a database and known to be representative of NSR or AF. The described method estimates the similarity between the standard density histograms and a test density histogram by the Kolmogorov-Smirnov (KS) test of the integral of the densities. The test density histogram is declared to evidence AF if it meets the KS test of not significantly different from the standard density histogram for AF.

Another technique used to reduce the data is to plot the data in some fashion that simplifies the interpretation of the data, e.g. as a Lorenz plot, which is a specific type of scatter plot. Such plots are a powerful graphic tool that can be applied to raw data to reduce the data to a form that can be more readily interpreted. There are various ways of identifying and selecting R-waves, processing the RR intervals and ΔRR intervals, displaying the Lorenz plots, and visually analyzing the Lorenz plots described in the prior art.

For example, such plotting process is described in U.S. Pat. No. 5,622,178, and in "Numeric Processing of Lorenz Plots of R-R Intervals From Long-term ECGs", by Hnatkova et al., *Journal of Electrocardiology*, Vol. 28 Suppl. pp. 74–80, 1995. In a Lorenz plot, the two successive RR intervals defined by three successive R-waves are defined as a "first RR interval" and a "second RR interval" and plotted in the 2-D scatter-plot as a data point of the scatter-plot. The first RR interval is the time between the first and second R-waves of the set of three R-waves, and the second RR interval is the time between second and third R-waves of the set of three R-waves. The first RR interval is plotted on one of the abscissa and the ordinate, and the second RR interval is plotted on the other of the abscissa and the ordinate. Assuming, for example, that the first RR interval is plotted on the ordinate, then the second RR interval is plotted on the ordinate. The first data point is then plotted at the intersection of the measured abscissa and ordinate within the 2-D field of the scatter-plot.

When the next succeeding or fourth R-wave is detected, the set of three R-waves is redefined as comprising the second, third and fourth R-waves, and the RR interval is measured between the third R-wave and the fourth R-wave. The "first RR interval" then becomes the time between the second and third R-waves, and the "second RR interval" becomes the time between the third and fourth R-waves. Based upon the above assumption, the newly defined first RR interval is plotted on the ordinate, and the second RR interval is measured on the abscissa. The second data point is then plotted at the intersection of the measured abscissa and ordinate.

The process then continues with each detected R-wave of the set to be plotted. The order of plotting each of the newly defined first and second RR intervals on the abscissa or ordinate reverses each time. The process continues for a predetermined time segment or number of R-waves.

Successively measured ΔRR values can be plotted in the same manner as RR intervals in a Lorenz plot. FIGS. 1A–1D are illustrative Lorenz plots of two-minute segments of ΔRR values that exhibit distributions of plotted data points that are characteristic of episodes of AF (FIG. 1A), NSR (FIG. 1B), AFL (FIG. 1C), and PVCs and/or PACs (FIG. 1D).

Beat-to-beat variability measure is used to generate Lorenz plots of RR intervals of collected ECG data as described in "Patterns of beat-to-beat variability in advanced heart failure", by Woo et al., *American Heart Journal*, Vol. 23, No. 3, pp. 704–710 (March, 1992).

Research has also been conducted to use such Lorenz scatter-plots of RR intervals from collected ECG data to illustrate episodes of AF affecting the RR intervals. See, for example, "Silent Zone on Lorenz Plots of the Ventricular Response Before Termination of Paroxysmal Atrial Fibrillation", by Nakatsu et al., *Japanese Circulation Journal*, Vol. 58, pp. 676–682, August, 1994, which contains a case report showing that in the patient, a specific pattern could be identified near the termination of AF. See also, "The Mechanism of the Silent Zone on Lorenz Plots in Atrial Fibrillation", *Roczniki Akademij Medycznej Bialymstoku*, by Pedich et al., Vol. 43, pp. 232–244, 1998, where it was demonstrated that the hypotheses in the case report by Nakatsu et al. was not valid when tested on more patients, i.e., the observed patterns did not correlate with the termination of AF. These references indicate how challenging the problem of determining AF can be. See also "Arrhythmia Analysis by Successive RR Plotting", by Anan et al., *Journal of Electrocardiology*, Vol. 23, No. 3, pp. 243–248, July, 1990. Here it is stated that a wide scattering of points in an Lorenz plot was diagnostic of AF; however, no method of determining this other than visually is described.

In the above-referenced '178 patent, techniques are disclosed for selecting which RR intervals are the most appropriate to include in a scatter-plot to present scatter-plot data in a manner that permits flexibility in the selection of analysis and display parameters. Minimum and maximum RR intervals are specified bounding the RR intervals that are included in a given scatter-plot. Moreover, the source of the heartbeats, such as normal and ectopic heartbeats, that are included in a scatter-plot are specified by a beat source analyzer in the system disclosed in the '178 patent.

To the inventor's understanding, the prior art does not appear to teach or disclose a method or structure for atrial arrhythmia detection and/or characterization by identifying formations in a scatter plot derived from ventricular beats.

There remains a need for algorithms for characterizing, discriminating, and detecting atrial arrhythmias and other cardiac physiological conditions, from ventricular episodes, beat-to-beat.

SUMMARY OF THE INVENTION

The present invention therefore provides algorithms for characterizing, discriminating and detecting atrial arrhythmia episodes within segments of ventricular cycle length data.

Different atrial arrhythmias and other cardiac physiological conditions display different patterns in a scatter plot. For example, episodes of AF often exhibit highly scattered (sparse) distributions, episodes of AFL often exhibit a highly condensed (clustered) distribution or formation, while normal sinus rhythm (NSR) would generally lie in between. In accordance with the present invention, metrics have been established to identify, discriminate and classify the various atrial arrhythmias and other cardiac physiological conditions. In the context of the present disclosure, the term "sparseness" is generally used to define a highly scattered distribution of data points in a plot. Further, the term "condensedness" is used to define conditions of data points that form one or more tight clusters.

In a Lorenz plot AF often appears as a very sparse distribution and NSR as a single tight cluster. Certain cardiac conditions, such as premature ventricular contractions (PVCs) can break this single cluster into a constellation of clusters. This can result in the NSR covering as large an area in the Lorenz plot as that of AF. However, AF and NSR with PVC's can be differentiated by the condensedness of the NSR cluster versus the sparseness of an AF distribution. Further, sinus tachyarrhythmia, which also presents a sparse distribution in the Lorenz plot, can be distinguished from AF using a sudden onset criterion as seen in AF.

The invention provides a set of algorithms each of which enable quantification of distribution formations that range from sparse to condensed. In this continuum, for example, AF is declared if the quantification/metric represents a more sparse condition than a predefined threshold and a sudden onset criterion is met. Similarly, AFl is declared if the quantification/metric represents a more condensed distribution relative to a predetermined threshold.

In certain embodiments, successive $\Delta RR$ intervals of a predetermined time segment of RR intervals are plotted in 2-D Lorenz plots, with $\Delta RR_i$ plotted along one axis and $\Delta RR_{i+1}$ plotted along the other axis. In one embodiment, a Nearest Neighbor Distance (NND) algorithm examines the distances between each distinct 2-D data point and its nearest neighbor 2-D data point and all these distances are summed to create an NND value. A high NND value corresponds to a high sparseness of the 2-D data points. In the alternate, a low NND value relates to a highly condensed distribution. An inverse NND or iNND discrimination metric can also be derived. A high iNND metric value signifies a high condensedness, a low iNND metric value signifies high sparseness.

In another embodiment, a Weighted Null Count (WNC) algorithm counts the number of neighboring 2-D data points within a local window of each distinct 2-D data point. A high value of a derived WNC metric signifies a high sparseness, and a low WNC metric value signifies a high condensedness. An inverse WNC metric (iWNC metric) algorithm develops an iWNC discrimination metric or iWNC metric from the same time-segment 2-D data points. A high value of the iWNC metric signifies a high condensedness, a low iWNC metric value signifies a high sparseness.

In another embodiment, the 2-D data points fall within predefined bins and are counted within each bin. In yet another embodiment, sparseness and condensedness are assessed.

In yet another embodiment, a Cluster Signature (CS) algorithm examines the condensedness or sparseness of 2-D data points about the origin and throughout the scatter-plot and develops a CS metric (CSM). The CSM is formulated from three factors: the maximum values of 2-D data points in any of the bins; the count of all bins that contain one or more data points; and, optionally, generating a 1-D histogram of the bin value in the 2-D bin count and summing across a predefined segment of the histogram values.

In a preferred embodiment of the CSM the need to count 2-D points is eliminated by using an indexing scheme that simulates the metrics implemented with assignment of data points in bins. In the CSM algorithm, there is no need to identify each bin that holds a 2-D data point or to identify the bin that holds the maximum number of 2-D data points by bin locations in the scatter-plot. The CSM is formulated from the maximum count of 2-D data points in a single bin, the number of bins holding at least one 2-D data point, and optionally including the sum of the content of a predefined set of bins.

The algorithms of the present invention can be employed to characterize, discriminate and detect episodes of atrial arrhythmias from the intervals between pressure signal pulses (PP and $\Delta PP$ intervals) signifying a ventricular cycle lengths rather than R-waves.

The present invention enhances and improves the detection capabilities of implantable therapy and monitoring medical devices. Specifically, the invention may be implemented in subcutaneous or submuscular sensing where noise and interference distort signals. It can also be used in external monitors, including event recorders and Holter monitoring systems, as well as in the Holter analysis software that is used to analyze a Holter recording.

The algorithms of the present invention can also be incorporated into a processor readable medium containing instructions to cause the processor to utilize ventricular signals to access atrial patterns for predicting, monitoring, diagnosing and treating atrial arrhythmias.

This summary of the invention including the features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIGS. 4, 6, 8, 10, 11 are specific embodiments of this universal scheme.

FIG. 8 is a flow chart illustrating the steps of processing a segment of ΔRR intervals utilizing the CS algorithm of the present invention to derive the CS discrimination metric and to determine whether the CS discrimination metric satisfies the AF signature metric or the AFL signature metric;

FIG. 10 is an alternative flow chart illustrating the derivation of the CS discrimination metric (or sub-metrics) and determination of whether it (or they) satisfies the AF signature metric or the AFL signature metric. This implementation is computationally highly efficient.

FIG. 11 is a flowchart for incorporating the sudden onset criterion for discrimination of AF episodes from highly irregular sinus tachycardia episodes. This criterion would work in conjunction with any of the previously-described AF or AFL detection schemes.

DETAILED DESCRIPTION OF THE
PREFERRED EMBODIMENTS OF THE
INVENTION

The algorithms of the present invention find particular utility embodied either in software or in firmware in cardiac EGM monitors that have EGM sense electrodes located within the patient's body either attached to the heart or located remote from the heart or a combination of both locations. The algorithms of the present invention can also be incorporated into software or in firmware of therapy delivery IMDs that would typically comprise a single chamber pacing system or ICD that senses the R-waves in the ventricles and delivers a pacing therapy or a cardioversion/defibrillation shock therapy to the ventricles. In that case, the algorithms of the present invention discriminate between high rate NSR based upon measured RR intervals and episodes of AF or AFL that are mistakenly detected as high rate NSR. However, it will be understood that the present invention is not so limited and that the algorithms of the present invention can be implemented into the firmware or software operating systems of external monitors having ECG electrodes coupled to the patient's skin to detect R-waves, e.g., Holter monitors, or within computerized systems that assess pre-recorded ECG or EGM data.

Figure 1A:
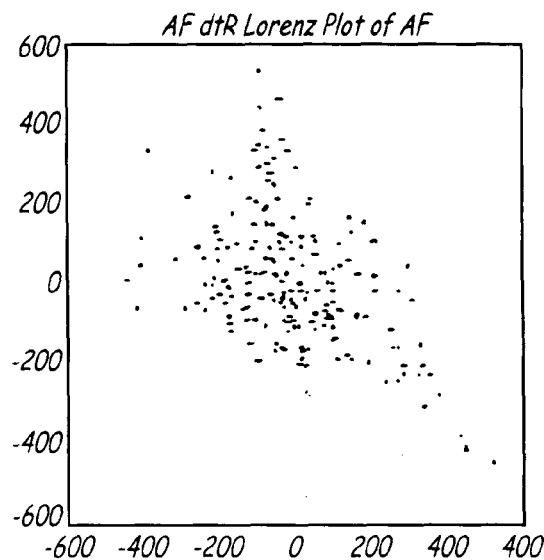
FIG. 1A is an illustrative scatter-plot of a two-minute segment of $\Delta RR$ values that exhibit distributions of plotted data points that are characteristic of episodes of AF.
Figure 1B:
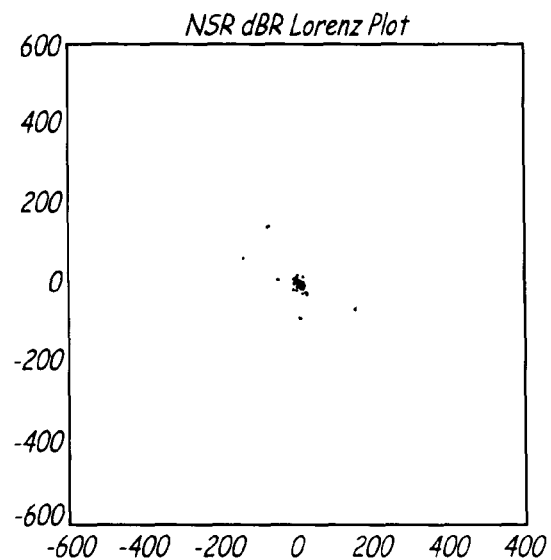
FIG. 1B is an illustrative scatter-plot of a two-minute segment of $\Delta RR$ values that exhibit distributions of plotted data points that are characteristic of a heart in NSR.
Figure 1C:
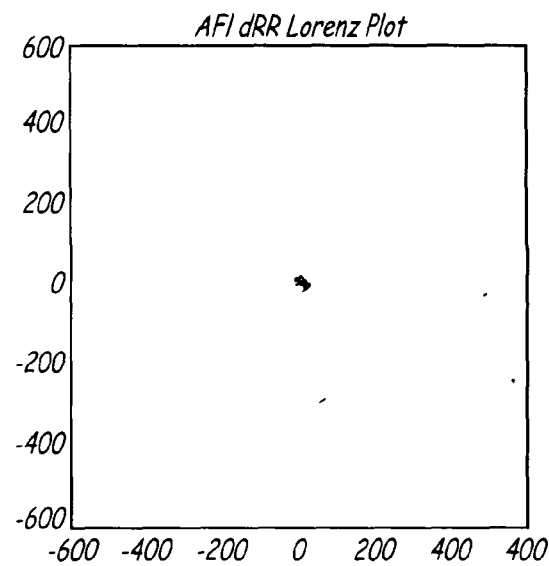
FIG. 1C is an illustrative scatter-plot of a two-minute segment of ΔRR values that exhibit distributions of plotted data points that are characteristic of episodes of AFL.
Figure 1D:
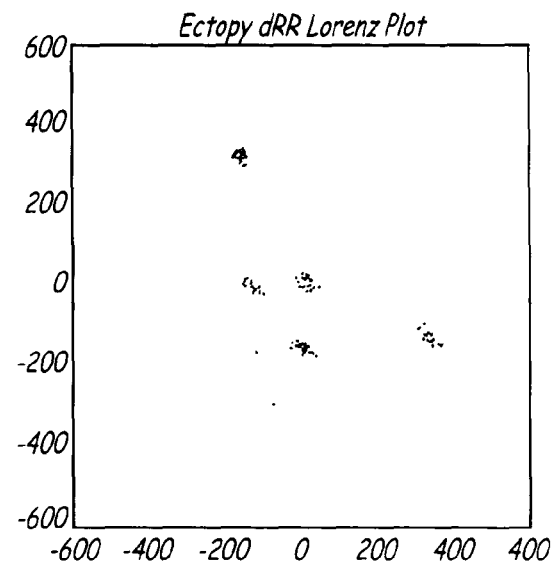
FIG. 1D is an illustrative scatter-plot of a two-minute segment of ΔRR values that exhibit distributions of plotted data points that are characteristic of occurrences of PVCs together with PACs.

The algorithms of the present invention were developed based on signature patterns observed in the Lorenz distribution of ΔRR intervals discriminating between NSR with or without PACs/PVCs and atrial tachyarrhythmias, particularly AF and AFL. The studies conducted in formulating the algorithms of the present invention focused upon developing easily implementable statistical measures or metrics which discriminate between AF episodes (FIG. 1A), NSR rhythm episodes (FIG. 1B), pure AFL episodes (FIG. 1C), and episodes containing PVCs and PACs (FIG. 1D). One observes a clustered nature of the variability of the plotted ΔRR points in FIGS. 1B, 1C, and 1D compared to the irregular variability of the plotted ΔRR points in FIG. 1A. The following described algorithms characterize the nature of the variability of the ΔRR intervals in a two-minute segment of RR intervals as AF when the ΔRR variability is irregular, i.e., sparse as in FIG. 1A, rather than clustered as in FIGS. 1B, 1C, and 1D. Moreover, the pure AFL episodes of FIG. 1C, which form very tight clusters, are also determined by employing the CS algorithm as described below and through inverse weighting steps in the NND and WNC algorithms as described below. In some cases of sinus tachycardia the ΔRR variability can be as irregular as shown in case of AF (FIG. 1A). Sudden onset criteria can be used in addition to discriminate such cases.

Figure 2:
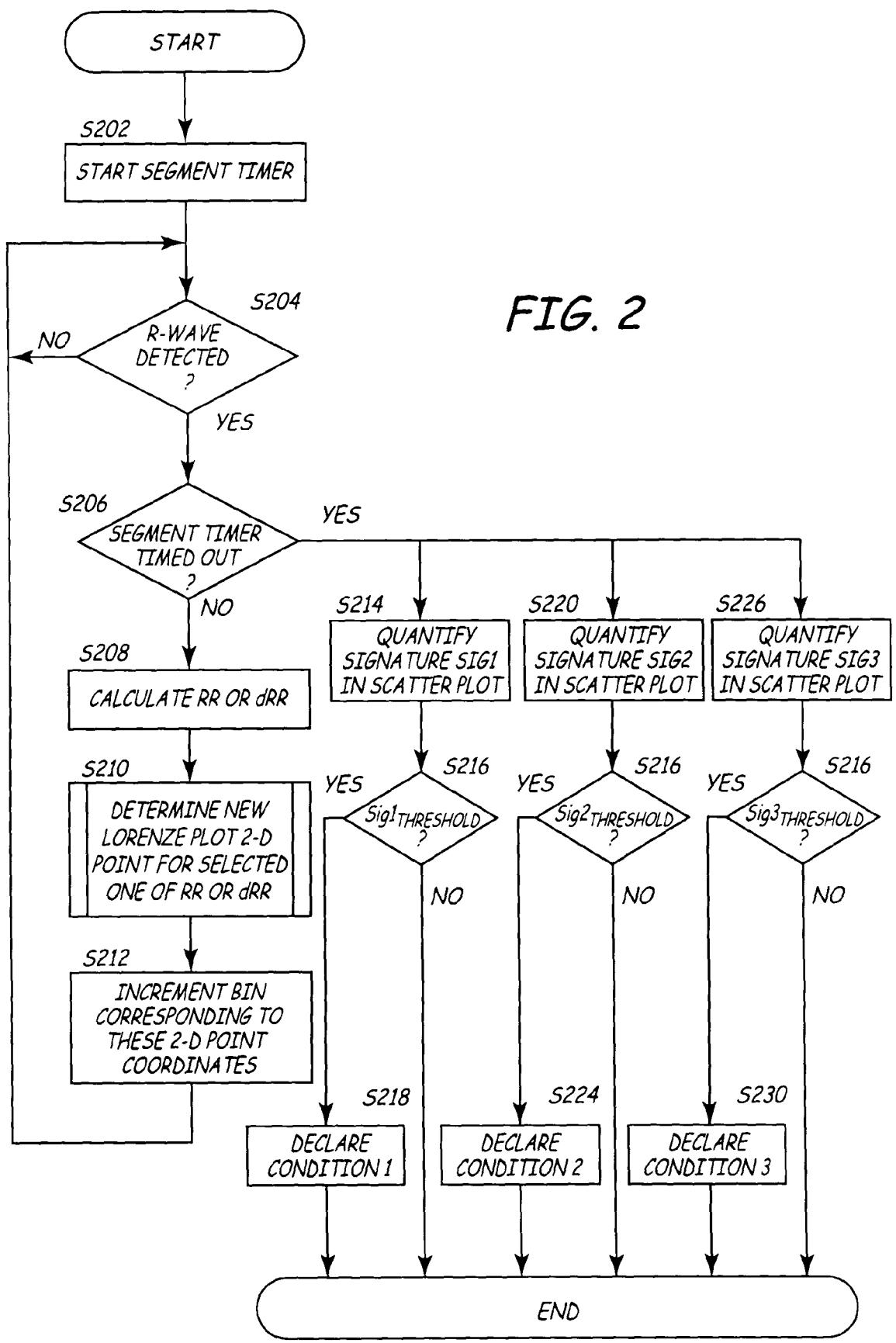
FIG. 2 is a flowchart illustrating the broad steps of quantifying different metrics from a scatter plot of segments of RR or ΔRR intervals and detecting different clinical conditions
Figure 3:
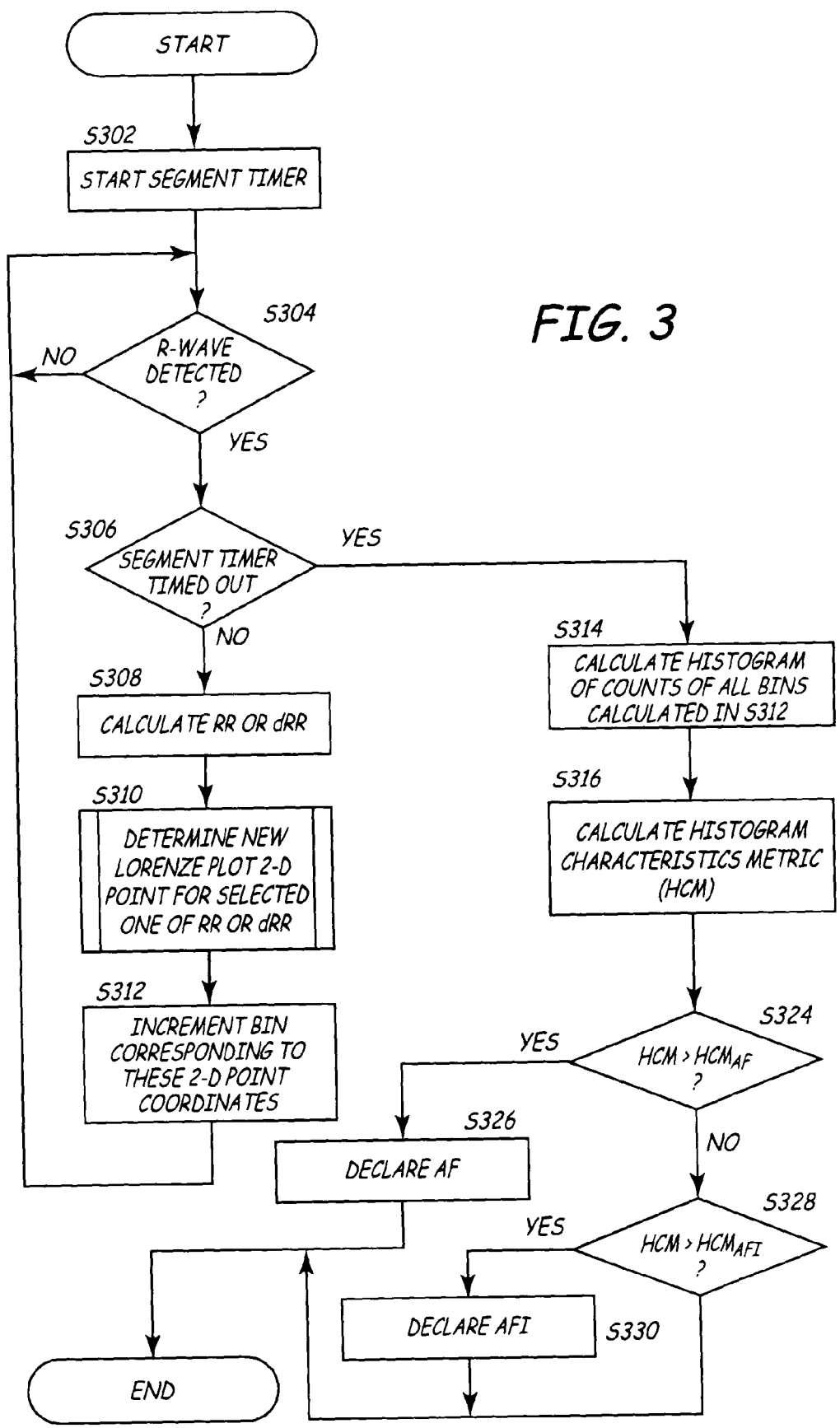
FIG. 3 is a flowchart illustrating how any Histogram Characteristic Metric can be derived and used to detect Atrial Tachycardias.

Each of the algorithms processes the two-minute segments of RR intervals to derive a "discrimination metric", that is a numeric value that is representative of the heart rhythms illustrated in FIGS. 1A–1D and described above. In addition, the discrimination metric is compared to a reference numeric value or "signature metric" for AF or AFL and AF or AFL is declared when the discrimination metric value satisfies the signature metric. FIG. 2 is a flowchart illustrating the broad steps of quantifying different metrics from a scatter plot of segments of RR or ΔRR intervals and detecting different clinical conditions from the signatures of these scatter plots. Each ventricular activation that is detected, such as the electrical detection of an R wave, is used to calculate the heart beat cycle length. From this the ΔRR can be calculated. Pairs or RR or ΔRR values are used to identify locations in a 2-D scatter plot, which are binned. The number of points that are counted in each of these bins is then the input into a signature metric quantification step or steps. Multiple of these steps can run using this same data, each designed to identify a specific signature. For example, one can be designed to identify atrial fibrillation and another atrial flutter; or a single signature metric can be used, for example, to identify only atrial fibrillation, or several metrics can be used, such as to identify frequent PVCs vs. atrial fibrillation vs. atrial flutter vs. sinus tachycardia. FIG. 3 is a flowchart illustrating how any Histogram Characteristic Metric can be derived and used to detect Atrial Tachycardias. FIGS. 4, 6, 8, 10, 11 are specific embodiments of this universal scheme.

Referring again to FIGS. 1A–1D, the Lorenz plot increases the dimensionality of the problem over using a 1-D distribution (the histogram of the RR or ΔRR intervals). The Lorenz plot makes use of the coupling between successive beats and thus gives a higher order of information. The Lorenz plot captures the information of how changes in one beat affect another. It allows one to represent successive ΔRR intervals, i.e., the difference between two successive measured RR intervals, as 2-D data points on the plot and to use spatial relationships between the 2-D data points to improve the discriminatory power of the algorithms. PVCs and PACs may have a repeated occurrence of the following sequence of RR intervals: normal, short, long, normal, short, long, etc. Thus, PVCs and PACs show up as tightly clustered points in a Lorenz distribution as shown in FIG. 1D that is not evident in any of the one-dimensional methods for measuring the variability of RR intervals. This increase in dimensionality of the representation allows for the improved discriminatory power of our AF detection algorithms from ectopic beats such as PVCs and PACs.

The Lorenz plot of ΔRR intervals over the two-minute segment of RR intervals is developed in the algorithms of the present invention because the ΔRR intervals enhance the discriminatory power of the algorithms when compared to using a Lorenz plot of RR intervals.

It is known that the variability of RR intervals, which can be approximated by the difference of the RR intervals, i.e., the ΔRR intervals, are larger in case of AF compared to NSR. Therefore, the Lorenz distribution of the ΔRR intervals provides better discriminatory power for detecting episodes of AF within or comprising an entire two-minute segment to the algorithms. The Lorenz distribution of ΔRR intervals uses the entire angular extent of the 2-D space to represent the data, i.e., it is an isotropic representation, and hence should provide a better representation of AF episodes than any other representation. An AF episode or a highly irregular sinus tachycardia episode appears as an isotropic cloud of 2-D data points as shown in FIG. 1A that differs markedly from the distributions of 2-D data points for NSR (FIG. 1B), AFL (FIG. 1C), and ectopic PVC or PAC beats (FIG. 1D). Similarly it is observed that AFL (FIG. 1C) appears as a very tight cluster about the origin when compared to the clusters for NSR (FIG. 1B) or the ectopic PVC or PAC beats (FIG. 1D).

In each of the algorithms of the present invention, the Lorenz plots of the 2-D data points have a defined origin, where ΔRR is zero, and are mathematically segmented into 2-D bins mapped as time interval segments of the full abscissa and ordinate +ΔRR intervals and −ΔRR intervals mapped from the origin. Thus, each 2-D data point falls within a bin, and, generally, the dispersion of 2-D data points among the total number of bins is employed in the algorithms to identify AF, sinus tachycardia, and/or AFL episodes.

In a monitor or therapy delivery IMD or a patient-worn external medical device, episode data and other measured physiologic data, if any, could be stored in memory with a time stamp for later uplink telemetry transmission in a telemetry session to an external medical device for display and analysis by a health care provider. Thus, only episode data relating to identified AF or AFL episodes is saved for such use. In a therapy delivery IMD, the declaration of AF or AFL can be employed to modify or inhibit delivery of a therapy designed to treat a declared ventricular tachyarrhythmia. These algorithms can also be employed in a computerized system for scanning previously recorded RR interval data to identify AF, sinus tachycardia, and AFL episodes in the data.

The NND algorithm examines the NND between each distinct 2-D data point and its nearest neighbor 2-D data point within a local window. Distance is weighted such that the NND of each 2-D data point, outside a certain defined distance from origin (DFO) criterion, is accorded a lower weight than the weight accorded the NND of each 2-D data point within the DFO criterion. The weighted NNDs are summed to develop an NND discrimination metric or NND metric. A high NND metric value signifies the likelihood of AF or sinus tachycardia, a lower NND metric value signifies the likelihood of NSR, and a very low NND metric value signifies a likelihood of AFL. The NND metric is compared to the AF signature metric (onset threshold) to determine if the NND metric satisfies the AF signature metric (onset threshold), and, if so, AF is declared. The AF signature metric in this case is referred to as an NND signature metric.

An inverse NND metric (iNND metric) algorithm develops an iNND of each 2-D data point from the same time-segment of 2-D data points and then reverses the weights applied to the iNNDs of the 2-D data points within the DFO criterion and outside the DFO criterion. The weighted iNNDs are summed to develop the iNND discrimination metric or iNND metric. A high iNND metric value signifies the likelihood of AFL, a lower iNND metric value signifies the likelihood of NSR, and a very, very low iNND metric value signifies a likelihood of AF. The iNND metric is compared to the AFL signature metric to determine if the iNND metric satisfies the AFL signature metric, and, if so, AFL is declared. In this case, the AFL signature metric is referred to as an iNND signature metric.

Figure 4A:
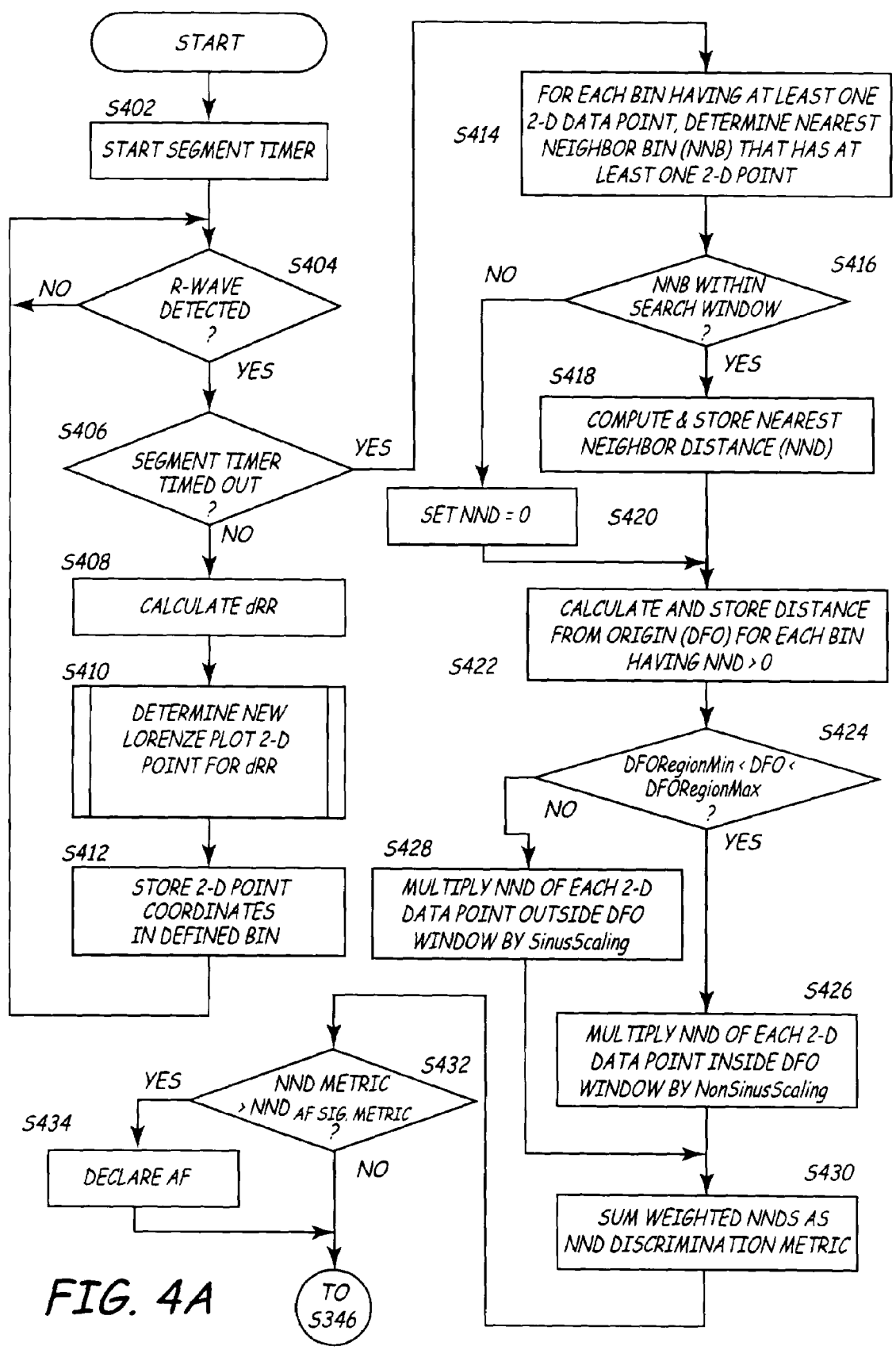
FIGS. 4A and 4B is a flow chart illustrating the steps of processing a segment of ΔRR intervals utilizing the NND algorithm of the present invention to derive NND and iNND discrimination metrics and determine whether the NND discrimination metric satisfies the AF signature metric or the iNND discrimination metric satisfies the AFL signature metric.
Figure 4B:
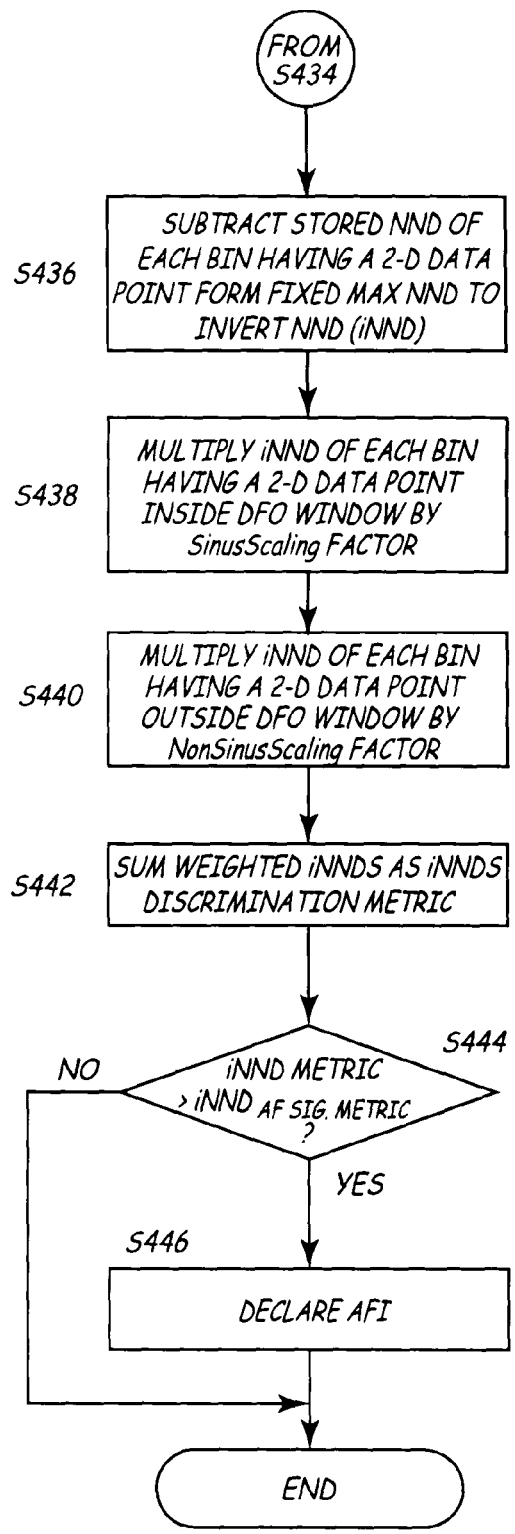
Figure 5:
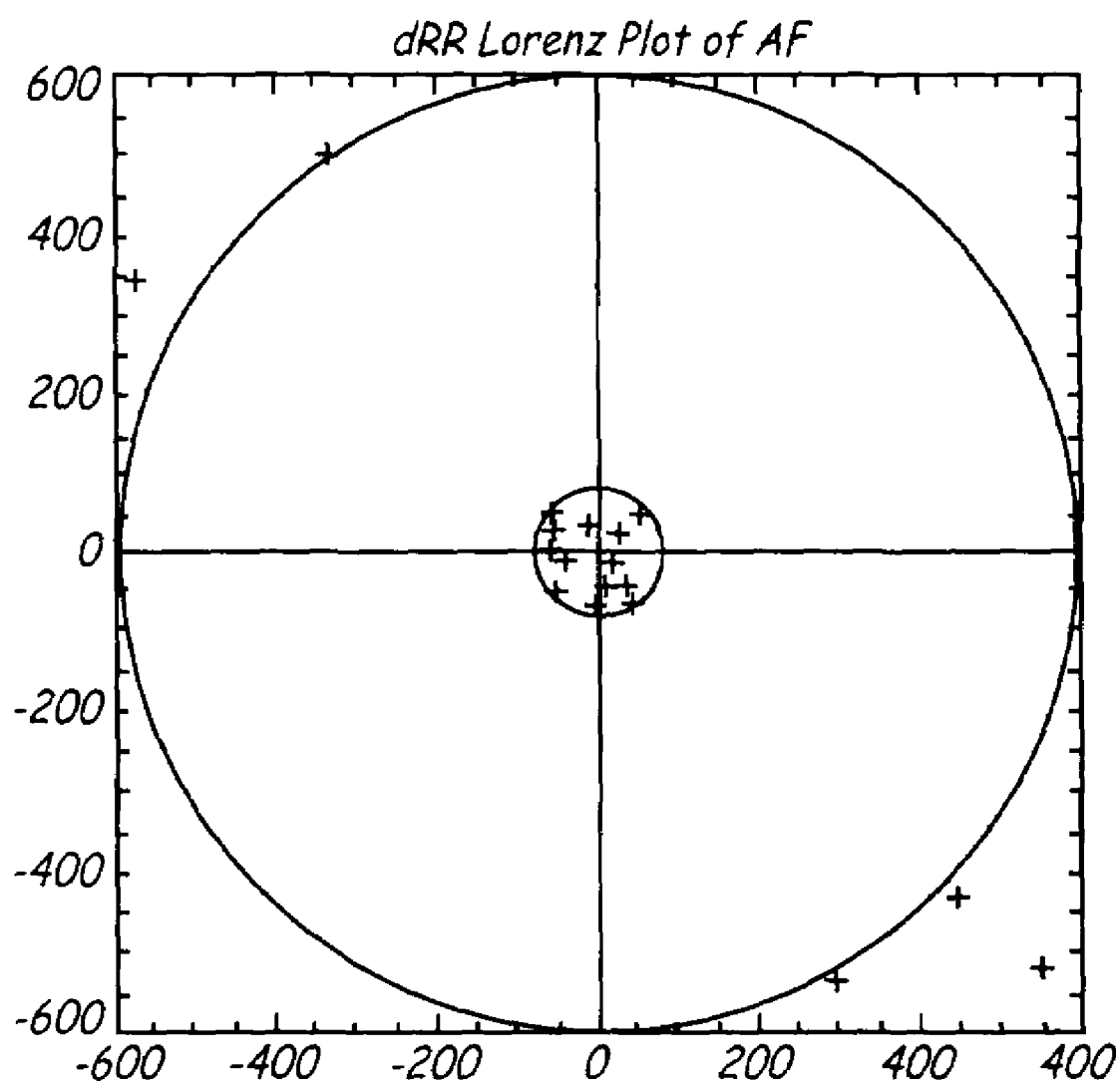
FIG. 5 is a Lorenz plot of a two-minute segment of ΔRR intervals evidencing an episode of AF and illustrating characterization steps of the NND algorithm of FIGS. 4A and 4B.

The NND algorithm illustrated in FIGS. 4A–4B and 5 thus quantifies the sparseness or texture or formations of the Lorenz distribution of ΔRR intervals over a time segment, e.g., a two-minute time segment. The NND algorithm identifies or declares episodes of AF in steps S414–S434 of FIG. 4A if the NND metric satisfies (exceeds in this example) the NND signature metric of sparseness. The NND algorithm continues in steps S436–S446 of FIG. 4B to identify or declare AFL if the iNND metric satisfies (exceeds in this example) an iNND signature metric of clustering.

The NND (AF) signature metric and iNND (AFL) signature metric can be derived a priori from confirmed episodes of AF and AFL in patient data specific to the patient following the NND algorithm of FIGS. 4A–4B and stored in memory of the IMD to be employed in the NND algorithm. Confirmed episodes of AF can be processed through steps S402–S430 of FIG. 4A to derive the NND signature metric, and confirmed episodes of AFL can be processed through steps S402–S442 of FIGS. 4A–4B to derive the iNND signature metric.

It should be noted that the order of examination of the data set of the two-minute segment to determine if it exhibits AF or AFL could be reversed in the NND algorithm of FIGS. 4A–4B. In addition, if one of AF or AFL, depending on the order, is first declared present in the data, then examination of the data to determine if it also satisfies the other of the AF or AFL signature metric can be bypassed. Furthermore, it will be shown that the steps of FIG. 4B can be performed simultaneously with certain steps of FIG. 4A to shorten processing time. In FIG. 4A, the Lorenz distribution of ΔRR intervals from each two-minute segment of RR intervals within 8 ms×8 ms bins is obtained in steps S402–S412. A relatively small bin size is employed in this case because it provides the maximum discrimination power as in case of an AF segment the bins will be filled with a few data points. Ideally, the bin size corresponds to the sampling interval of the EGM to provide maximum discrimination. However, the number of bins increases as bin size is decreased, and the time for computation also increases proportionally. When the two-minute time segment is timed out, each bin incremented in step S412 contains zero or one or more than one 2-D data point(s). The sequence of steps S402–S412 is merely illustrative of one way of accumulating the ΔRR intervals within the defined bins of the Lorenz plot shown in FIG. 5, and the NND algorithm can be performed using alternative and equivalent steps of accomplishing the same.

Then, the NND between 2-D data points in different bins and within a local window is determined in steps S414 through S418. The local window is of a predetermined or programmed size, e.g., 80 ms, exceeds the bin size, but is less than the full size of the Lorenz plot. If the NND exceeds this local window, then it is assumed that the particular 2-D point, not having a neighboring 2-D data point within the local window, represents noise. The size of the local window may be made programmable and is selected empirically to reflect a given patient's exposure to ambient noise and/or the propensity of the implanted system to mistakenly detect noise as an R-wave, which can be determined in a patient work-up. The window size is chosen based on prior knowledge obtained from observing the average distance between points in the Lorenz distribution of ΔRR intervals of AF segments. The Euclidean (geometric) distance in a 2-D space is thus computed between each 2-D data point and it's found nearest neighbor 2-D data point within the 80 ms local window. If more than one 2-D data point is within a single bin of the Lorenz plot, then, the NND between those 2-D data points is zero and is effectively not factored into the determination of the NND metric. Similarly, while there may be one or more 2-D data point within a single bin having a measurable NND, it is so small as to not appreciably increment the NND metric.

Next, the measured NND for each 2-D data point is weighted depending on how far the 2-D data point is from the origin in the Lorenz plot. Any 2-D data points that are less than a minimum distance DFORegionMin, e.g., 50 ms, or more than a maximum distance DFORegionMax, e.g. 750 ms, away from the origin are considered less likely to be from an AF episode. Those 2-D data points within 50 ms from the origin are more likely due to NSR or AFL, and those 2-D data points farther than 750 ms from the origin are more likely due to erroneous detection of noise. Note that the minimum and maximum distances of the DFO criterion can be varied and that FIG. 5 depicts a differing maximum distance of 600 ms appropriate to the scale of illustration in FIG. 5. Thus, the distance from the origin (DFO) of each 2-D data points satisfying the local window criteria in step S416 is identified in step S220 and compared to the minimum and maximum distance in step S422. Any such NND that falls within the 50 ms–750 ms DFO window is given a greater weight than any such NND that falls outside the DFO window. In step S424, any such NND that falls within the 50 ms–750 ms DFO window is multiplied by NonSinusScaling, e.g. 1.0, and in step S426, any such NND that falls outside the 50 ms–750 ms DFO window is multiplied by SinusScaling, e.g. 0.1, in step S228. The DFO weighting is a way of incorporating some a-priori knowledge to improve the discrimination power of the NND algorithm. The factors 1.0 and 0.1 are selected based on observations of approximate likelihood of data points occurring in those regions. However, any weighting factors can be assigned depending upon the requirements.

The weighted NNDs are then summed in step S430 to derive the NND metric for the two-minute segment of RR intervals. A large NND metric signifies that the two-minute segment comprises or includes an AF episode. The NND metric is high if a significant portion of the two-minute segment of RR data is in AF. A very low value of the summed NND metric signifies that the two-minute segment comprises NSR. A low to medium value of the summed NND metric signifies that the two-minute segment contains PVCs and/or PACs conducted to the ventricles. A medium value of the summed NND metric signifies a sinus tachycardia episode. If the summed NND metric approaches zero, it signifies that the two-minute segment comprises AFL.

In a monitor or therapy delivery IMD or a patient-worn external medical device, the NND metric is compared to a threshold value for AF in step S432. AF is declared in step S434 if the threshold value is exceeded in step S432. Then, the episode data and other measured physiologic data, if any, could be stored in memory with a time stamp for later uplink telemetry transmission in a telemetry session to an external medical device for display and analysis by a health care provider. Thus, only episode data relating to identified AF episodes is saved for such use. The NND algorithm can also be employed in a computerized system for scanning previously recorded RR interval data to identify AF episodes in the data.

In this form, the NND metric does provide significant discriminatory power between AF episodes and non-AF episodes, but it does not provide enough discrimination between AFL and non-AFL episodes. The declaration of AFL is preferably dependent upon satisfaction of the AFL signature metric in step S444 as described below. It is possible to condition the performance of steps S436–S446 upon a determination that the summed NND metric is lower than a conditional AFL signature metric. Steps S436–S446 employ the NND of each 2-D data point stored in step S418. In step S436, the stored NND of each bin having a 2-D data point determined in step S418 is subtracted from a maximum NND that can be selected to be greater than the maximum DFO of the plot to provide the iNND. Then, the DFO of the 2-D data point stored in step S422 is employed to determine if the 2-D data point is within or outside the DFO window per step S424. The iNND of each bin having a 2-D data point inside the DFO window is multiplied by a SinusScaling factor of 0.1 in step S438, whereas the iNND of each bin having a 2-D data point outside the DFO window is multiplied by a NonSinusScaling factor of 1.0 in step S440. Each data point iNND is weighted according to the DFO criterion and summed to obtain the iNND metric in step S442. In this case the weighting factors are reversed. A lower weight is applied to the iNNDs for 2-D data points, which meet the DFO criterion, whereas a higher weight is applied to the iNNDs for 2-D data points not meeting the DFO criterion.

The iNND metric is compared to the iNND signature metric in step S444, and AFL is declared in step S446 if the iNND metric satisfies the iNND signature metric. A high value for the iNND metric is characteristic of a very tightly clustered Lorenz distribution, as in case of tight AFL as illustrated in FIG. 1B. The value for the iNND metric decreases as the tightness of a cluster decreases. The value of the iNND metric is medium or low for NSR segments. An AF segment as shown in FIG. 1A is not clustered at all, and hence the iNND metric will be a very, very low value for an AF segment. Here again, the iNND metric discriminates well between regular AFL and irregular AF segments and does not discriminate well between AF and non-AF segments. Further the iNND metric may be computed for smaller (less than 2 min. as in S406) segments of data to detect smaller true AFL episodes.

Thus, the NND metric provided by the NND algorithm in step S430 comprises a numeric value that is relatively higher when the 2-D data points of the Lorenz plot are sparser and less clustered. Correspondingly, the iNND metric provided in step S442 has a numeric value which is relatively higher when the 2-D data points of the Lorenz plot are very tightly clustered. In case the Lorenz distribution is very sparse (as in case of AF), then the NND metric will be large and the iNND metric will be very, very small. Conversely, the iNND metric will be very, very large for an AFL segment, and very, very small for an AF segment. Both the NND metric and the iNND metric will have small to medium values if the Lorenz distribution or formation of 2-D data plots represents NSR or PVCs/PACs It should be apparent from the above that step S436 can be performed between steps S418 and S422 and the iNND stored as steps S422 and S424 are performed. Then, steps S438–S446 can be performed in parallel with steps S426–S434.

The Windowed Null Count (WNC) algorithm counts the number of neighboring 2-D data points within a local window of each distinct 2-D data point to obtain a Point Count. The Point Count is subtracted from a large constant number representing the maximum number of 2-D data points that could be within the local window to obtain a Null Count. The Null Count of each distinct 2-D data point is weighted in accordance to the DFO criterion, in which a higher weight is applied to the NC of the 2-D data point that satisfies the DFO criterion and a lower weight is applied to the NC of the 2-D data point that does not satisfy the DFO criterion. The Weighted Null Count (WNC) thus obtained for each 2-D data point is summed for all distinct 2-D data points in the time segment to obtain the WNC discrimination metric or WNC metric. A high WNC metric value signifies the likelihood of AF, and a low WNC metric value signifies the likelihood of NSR. The WNC metric is designed to maximize the discriminatory power between AF and non-AF segments. The WNC metric is compared to the AF signature metric to determine if the WNC metric satisfies the AF signature metric, and, if so, AF is declared. In this case, the AF signature metric is also referred to as the WNC signature metric.

A very low value of the WNC metric signifies higher likelihood of AFL; however, this low value of the WNC metric does not have enough discriminatory power to detect AFL. An inverse WNC metric (iWNC metric) algorithm develops an iWNC discrimination metric or iWNC metric from the same time-segment 2-D data points by applying the weights in reverse order to the Point Count of 2-D data points within the DFO criterion and outside the DFO criterion to develop an Weighted Point Count (WPC). The WPC of all of the 2-D data points are summed to form an iWNC or WPC discrimination metric or WPC metric. A high value of the WPC metric signifies the likelihood of AFL, a lower WPC metric value signifies the likelihood of NSR, and a very, very low WPC metric value signifies a likelihood of AF. The WPC metric is compared to the AFL signature metric to determine if the WPC metric satisfies the AFL signature metric, and, if so, AFL is declared. The AFL signature metric is also referred to as a WPC signature metric in this case The WNC algorithm illustrated in FIGS. 6A–6B and FIG. 7 thus quantifies formations exhibiting sparseness or clustering in the distribution of the ΔRR intervals plotted as 2-D data points of a Lorenz plot over a time segment. Note that the minimum and maximum distances of the DFO criterion can be varied and that FIG. 7 depicts a differing maximum distance of 600 ms appropriate to the scale of illustration in FIG. 7.

Figure 6B:
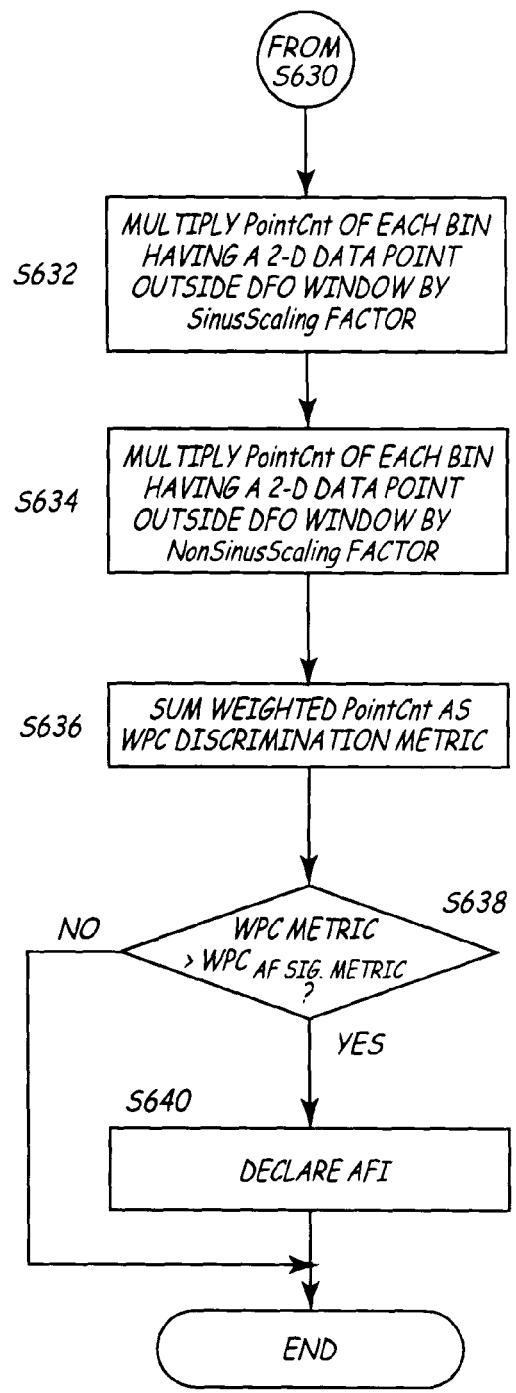
FIGS. 6A and 6B is a flow chart illustrating the steps of processing a segment of ΔRR intervals utilizing the WNC algorithm of the present invention to derive WNC and iWNC or WPC discrimination metrics and determine whether the WNC discrimination metric satisfies the AF signature metric or the WPC discrimination metric satisfies the AFL signature metric.
Figure 6A:
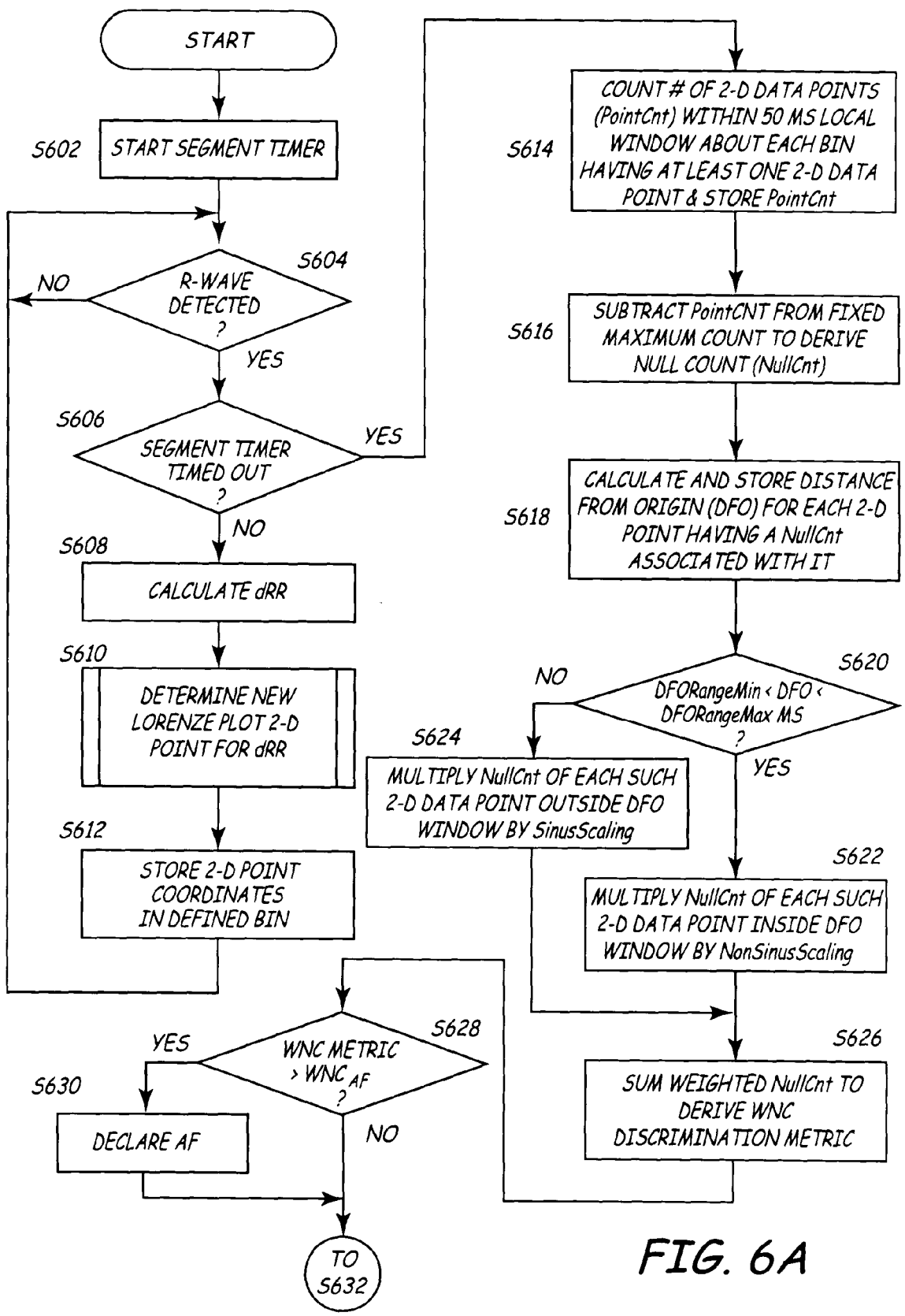
Figure 7:
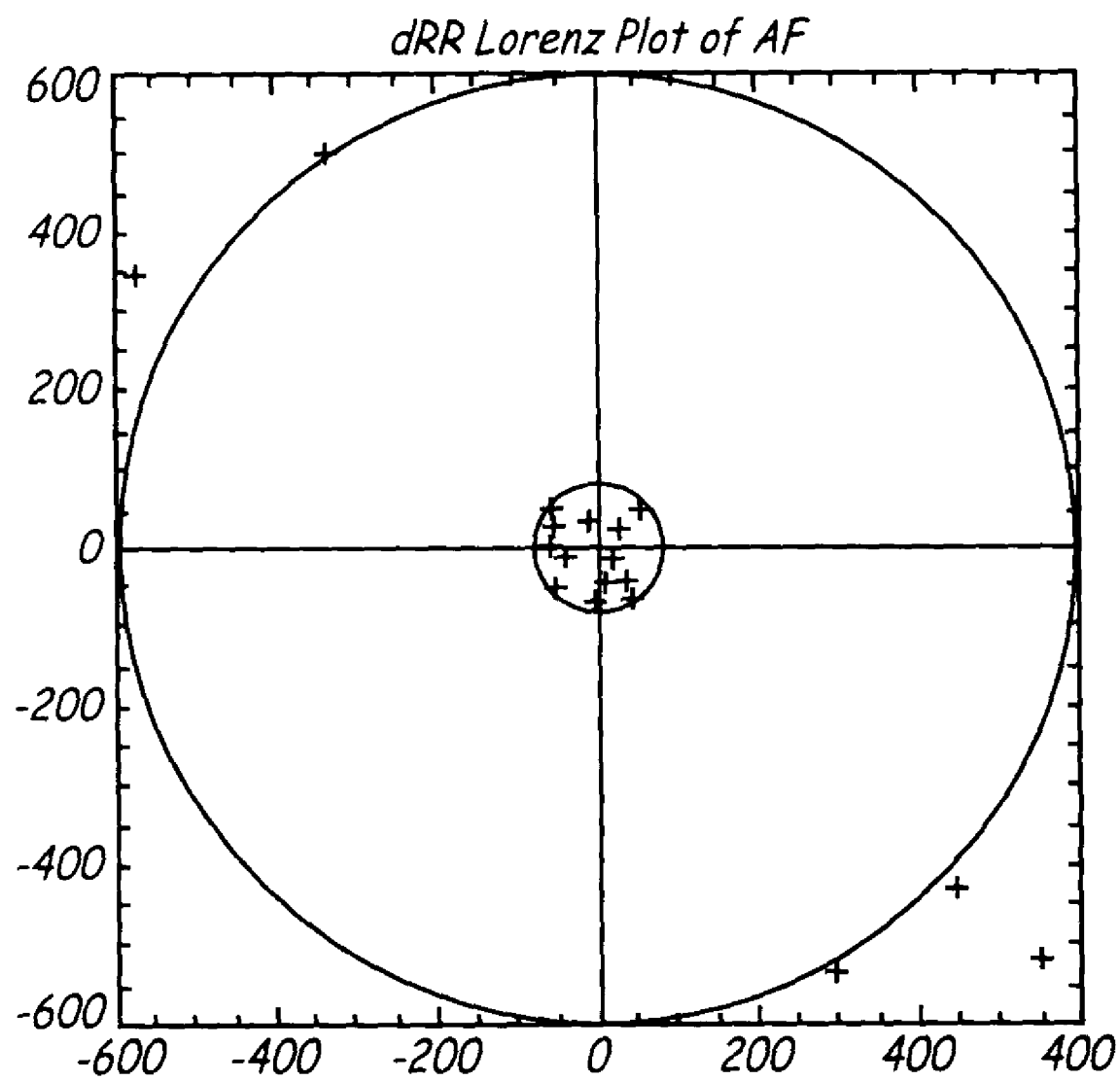
FIG. 7 is a Lorenz plot of a two-minute segment of ΔRR intervals evidencing an episode of AF and illustrating characterization steps of the WNC algorithm of FIGS. 4A and 4B.

The Lorenz distribution of ΔRR intervals from two-minute segments of data is obtained using 20 ms bins along each axis as shown in FIG. 7. Thus, steps S602–S612 of FIG. 6A are performed in the manner described above for steps S402–S412, except that the bin size is 20 ms×20 ms in this algorithm. The 20 ms bin size was found to be optimal to provide maximum discrimination between AF and non-AF episodes and is sufficient to enable maximum discrimination between AFL and non-AFL episodes The WNC algorithm identifies or declares episodes of AF in steps S614–S630 of FIG. 6A if the WNC metric satisfies (exceeds in this example) an AF signature metric of sparseness. The WNC algorithm continues in steps S632–S640 of FIG. 6B to identify or declare AFL if the iWNC or WPC metric satisfies (exceeds in this example) the WPC signature metric of clustering.

The WNC (AF) signature metric and WPC (AFL) signature metric can be derived a priori from confirmed episodes of AF and AFL in patient data specific to the patient and stored in memory of the IMD to be employed in the WNC algorithm. Confirmed episodes of AF can be processed through steps S602–S626 of FIG. 6A to derive the WNC signature metric, and confirmed episodes of AFL can be processed through steps S602–S636 of FIGS. 6A–6B to derive the WPC signature metric.

It should be noted that the order of examination of the data set of the two-minute segment to determine if it exhibits AF or AFL can be reversed in the WNC algorithm of FIGS. 6A–6B. In addition, if one of AF or AFL, depending on the order, is first declared present in the data, then examination of the data to determine if it also satisfies the other of the AF or AFL signature metric can be bypassed. Furthermore, it will be shown that the steps of FIG. 6B can be performed simultaneously with certain steps of FIG. 6A to shorten processing time.

For each 2-D data point in the ΔRR Lorenz distribution illustrated in FIG. 7, the number of bins having at least one 2-D data point within a local window distance less than a selected distance, e.g., 50 ms, from that 2-D data point is computed as a Point Count (PointCnt) for that 2-D data point. The Null Count (NullCnt) is derived in step S616 by subtracting each PointCnt from a fixed maximum count, which is some number larger than the maximum possible PointCnt. The NullCnt for each 2-D data point is weighted in steps S620–S622 and summed in step S626 to obtain a WNC metric for the two-minute segment.

Multiple 2-D data points in a single bin are not considered distinct during the summation procedure of step S626. If a 2-D data point is not distinct, i.e. more than one pair of ΔRR intervals have the same values in that two-minute segment, then the WNC for each of those non-distinct 2-D data points will be the same. For NSR, PVCs and PACs, which appear clustered in the Lorenz plot distribution, there is a higher probability of having a lesser number of distinct points in the Lorenz distribution, and hence a lesser effective number of 2-D data points if non-distinct points are considered as only one 2-D data point. The discriminatory benefit of using distinct points will be evident in later steps of this algorithm. However, it needs to be noted that, for counting the total number of neighboring points about a local window of each distinct 2-D data point, one needs to count all 2-D data points including the extra non-distinct 2-D data points.

First, a local window of 50 ms around each 2-D data point is defined, and the number of bins within 50 ms of each distinct 2-D data point is determined in step S614. In step S614, the NullCnt for the distinct 2-D data point is computed by counting the total number of neighboring 2-D data points, including non-distinct 2-D data points, within the local window about the 2-D data point as a Point Count (PointCnt). Then, that PointCnt of neighboring 2-D data points is subtracted from a large constant number which should be greater than the maximum possible neighboring points in that local window to obtain the NullCnt for the distinct 2-D data point being examined. The NullCnt for the 2-D data point is thus an arbitrary number that is very close to the maximum possible number if the actual PointCnt of neighboring 2-D data points approaches zero, signifying that the window is sparsely populated with 2-D data points.

An optimal local window size is obtained based on performance of the algorithm on a test data set. Applying the local window improves the discrimination ability between a sparse distribution and a clustered distribution. For example, if no local window is used, then the neighbor count for each distinct 2-D data point will consist of all the 2-D data points in the Lorenz plot of FIG. 5, and the resulting WNC metric would I lose the discriminatory power to distinguish between a sparse distribution and a clustered distribution.

Therefore, the NullCnt determined in step S616 is large if the Lorenz distribution is very sparse as in case of AF. In the present context, sparseness is used to mean uniformly distributed, i.e., a lower number of points per unit area in Lorenz space wherever 2-D data points are present. For NSR, PVCs and PACs, which appear clustered (more number of points per unit area) in the Lorenz distribution, the neighbor counts will be large, and hence WNC will be small for each 2-D data point compared to a sparse case.

As in the NND algorithm, any 2-D data point that is outside a DFO window that is less than a minimum DFO DFORegionMin, e.g., 50 ms, or more than a maximum DFO DFORegionMax, e.g. 750 ms, is considered less likely to be from an AF episode. Therefore, the DFO for all such 2-D data points having a NullCnt associated with it is determined in step S618 and compared to the upper and lower bounds of the DFO window in step S620. The NullCnt associated with such 2-D data point that falls within the 50 ms 750 ms DFO window is given a greater weight than the NullCnt of any such 2-D data point that falls outside the DFO window. Any such NullCnt that falls within the 50 ms–750 ms DFO window is multiplied by NonSinusScaling, e.g. 1.0, in step S622, and any such NullCnt that falls outside the 50 ms–750 ms DFO window is multiplied by SinusScaling, e.g. 0.1, in step S624.

Again, the DFO weighting is a way of incorporating some a-priori knowledge to improve the discrimination power of the NND algorithm. Again, the factors 1.0 and 0.1 are selected based on observations of approximate likelihood of data points occurring in those regions. However, any weighting factors can be assigned depending upon the requirements. The NullCnts are summed in step S626 to provide the WNC metric. A large WNC metric signifies that the two-minute segment comprises or includes an AF episode. A low value of the summed WNC metric signifies that the two-minute segment comprises NSR. A low to medium value of the summed WNC metric signifies that the two-minute segment contains PVCs and/or PACs conducted to the ventricles. If the summed WNC metric approaches zero, it signifies that the two-minute segment comprises AFL. However this cannot be used to discriminate between AFL and non-AFL episodes. In a monitor or therapy delivery IMD or a patient-worn external medical device, the WNC metric is compared to a WNC signature metric for AF in step S628. AF is declared in step S630 if the threshold value is exceeded in step S628. Then, the episode data and other measured physiologic data, if any, is preferably stored in memory with a time stamp for later uplink telemetry transmission in a telemetry session to an external medical device for display and analysis by a health care provider. Thus, only episode data relating to identified AF episodes is saved for such use. The WNC algorithm can also be employed in a computerized system for scanning previously recorded RR interval data to identify AF episodes in the data.

A complementary iWNC or WPC algorithm develops a WPC metric that provides for the discrimination between AFL and non-AFL segments as shown in steps S632–S640 of FIG. 6B. The PointCnt stored in step S614 and the DFO of the 2-D data point stored in step S618 are employed in steps S632 and S634 to derive a weighted PointCnt or WPC for each 2-D data point. The PointCnt of each bin having a 2-D data point inside the DFO window is multiplied by a SinusScaling factor of 0.1 in step S632, and the PointCnt of each bin having a 2-D data point outside the DFO window is multiplied by a NonSinusScaling factor of 1.0 in step S634.

The WPC metric is compared to the WPC signature metric in step S638, and AFL is declared in step S640 if the WPC metric satisfies the AFL signature metric. A high value for the WPC metric is characteristic of a very tightly clustered Lorenz distribution, as in case of tight AFL as illustrated in FIG. 1B. The value for the WPC metric decreases as the tightness of a cluster decreases. The value of the WPC metric is medium or low for NSR segments. An AF segment as shown in FIG. 1A is not clustered at all, and hence the WPC metric will be a very, very low value for an AF segment. Here again, the WPC metric discriminates well between regular AFL and irregular AF segments and does not discriminate well between AF and non-AF segments. Further the WPC metric may be computed for smaller (less than 2 min. as in S606) segments of data to detect smaller true AFL episodes.

Thus, the WNC metric provided by the WNC algorithm in step S626 comprises a numeric value that is relatively higher when the 2-D data points of the Lorenz plot are sparser and less clustered. Correspondingly, the WPC metric provided in step S636 has a numeric value that is relatively higher when the 2-D data points of the Lorenz plot are very tightly clustered. If the Lorenz distribution is very sparse (as in case of AF), then the WNC metric will be large and the WPC metric will be very, very small. Conversely, the WPC metric will be very, very large for an AFL segment, and very, very small for an AF segment. Both the WNC metric and the WPC metric will have small to medium values if the Lorenz distribution or formation of 2-D data plots represents NSR or PVCs/PACs. It should be apparent from the above that steps S632–S640 can be performed in parallel with steps S624–S630.

The Cluster Signature (CS) algorithm examines the concentration or sparseness of 2-D data points about the origin and throughout the scatter-plot. The number of 2-D data points in each bin is counted and compared to determine the number of bins containing at least one 2-D data point (nZeroCnt), the maximum number of 2-D data points in a single bin (MaxVal), and optionally counting the number of bins containing 1 to N 2-D data points (loCnt). The CS metric (CSM) is derived from the combination of nZeroCnt, MaxVal and (optionally) loCnt or the individual comparison of nZeroCnt and MaxVal to AF and AFL signature metrics, respectively. When loCnt and/or nZeroCnt are high and MaxVal is low, the combined CSM or nZeroCnt satisfies an AF signature metric ($CSM_{AF\ SIG.\ METRIC}$). When loCnt and/or nZeroCnt are low and MaxVal is high, the combined CSM or MaxVal satisfies an AFL signature metric ($CSM_{AFL\ SIG.\ METRIC}$).

Figure 8:
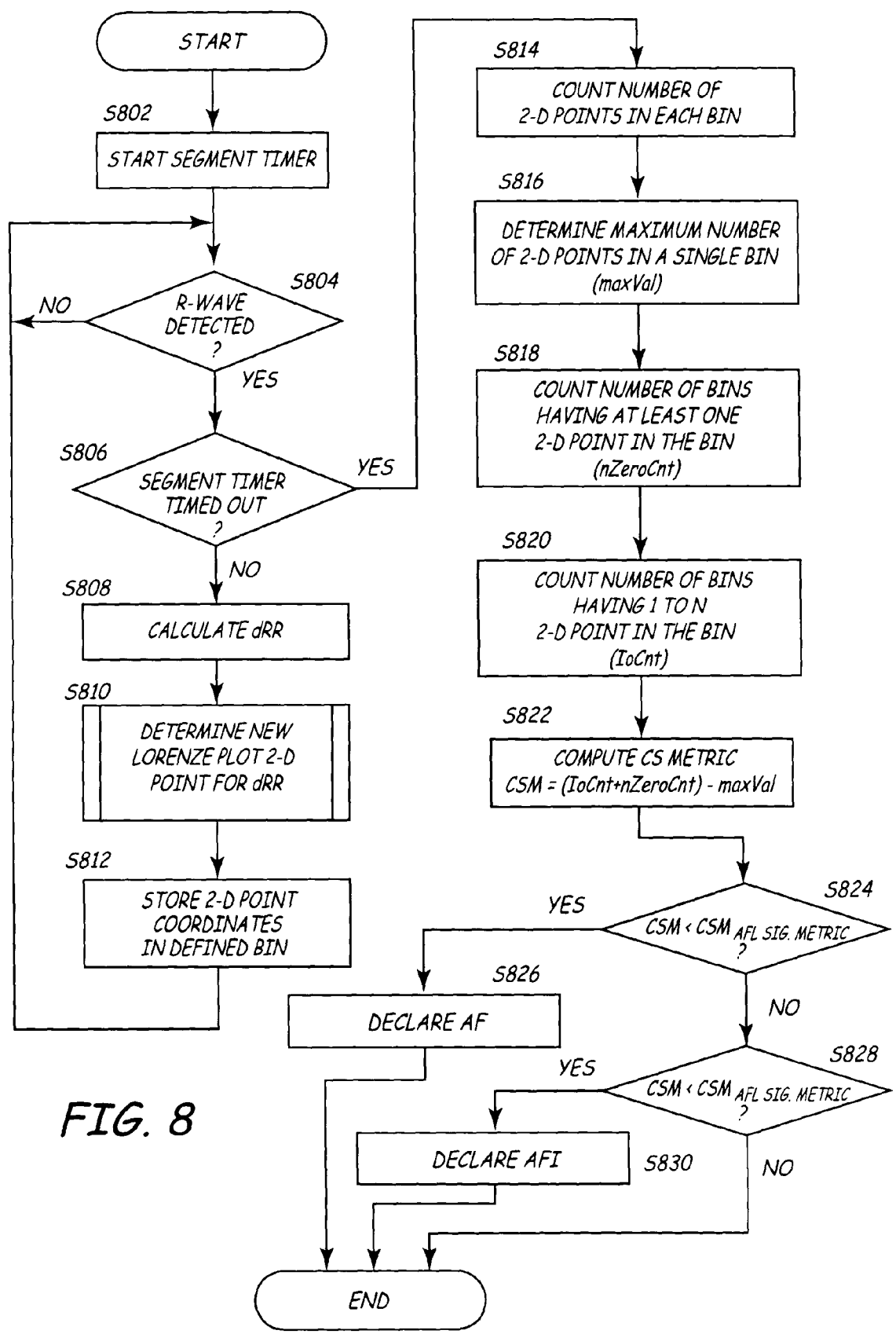
Figure 9:
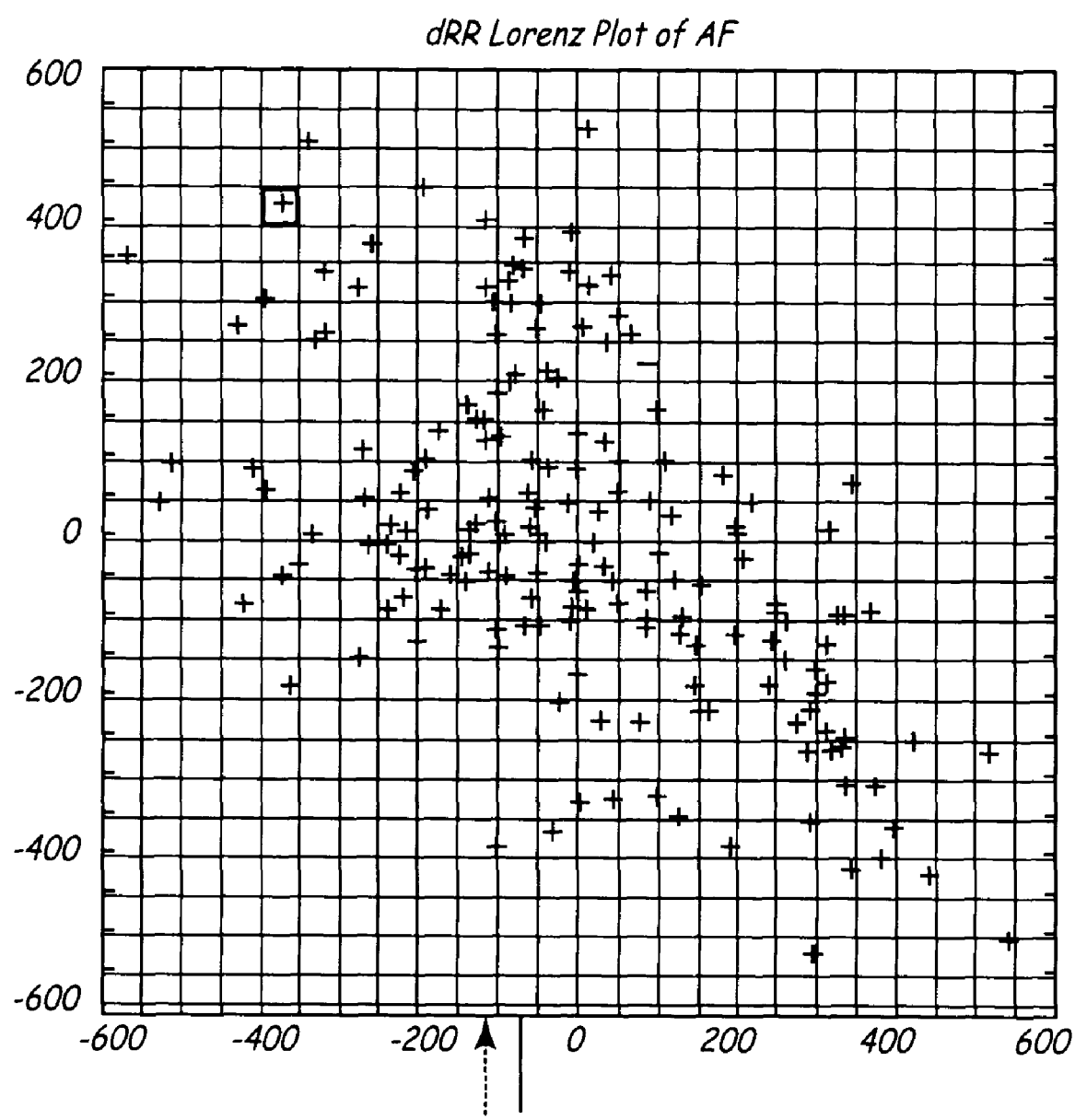
FIG. 9 is a Lorenz plot of a two-minute segment of ΔRR intervals evidencing an episode of AF and illustrating characterization steps of the CS algorithm of FIG. 6.
Figure 10:
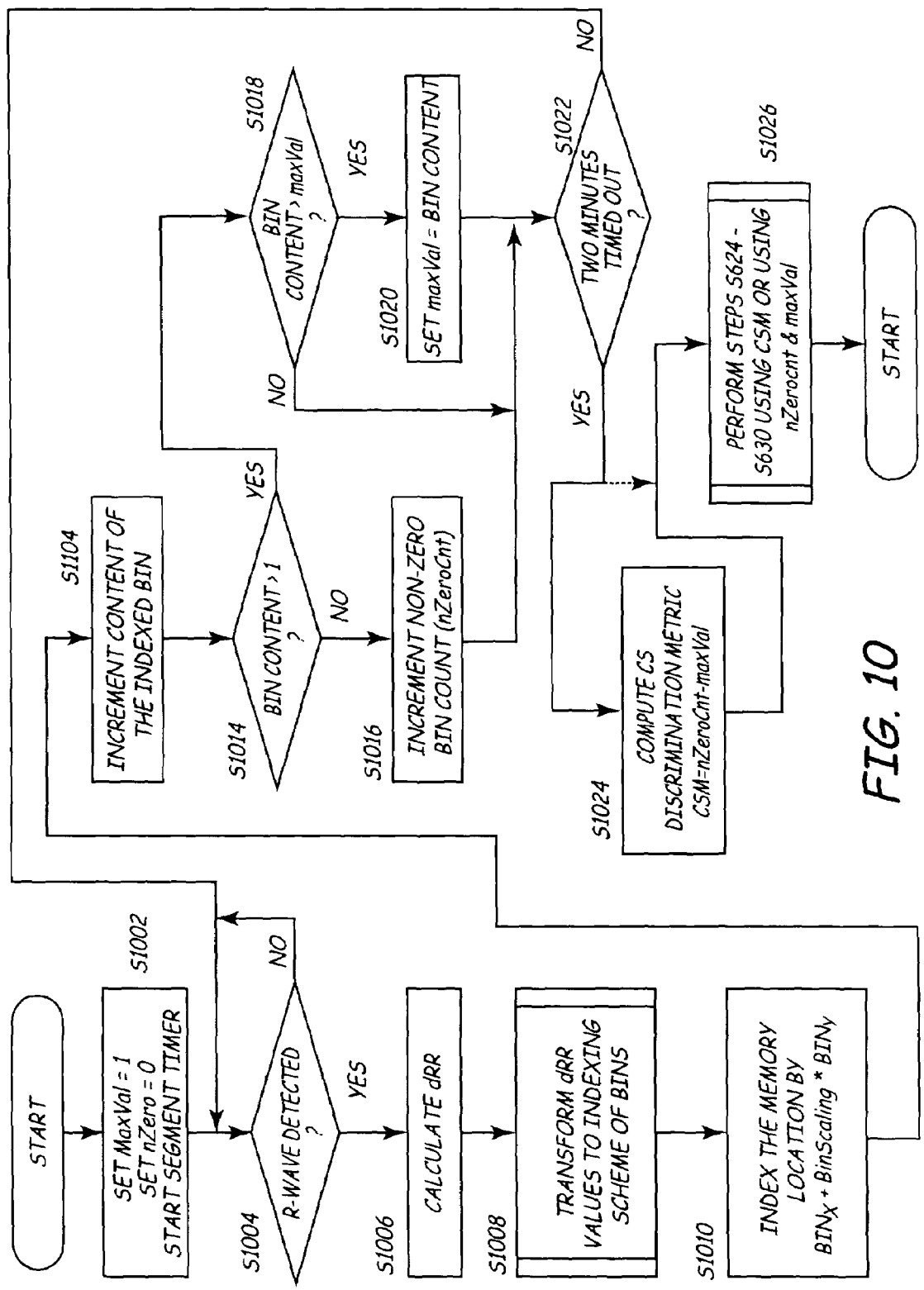

The CS algorithm illustrated in FIGS. 8–10 is similar in nature to the NND and the WNC algorithms but is superior to them in terms of computational complexity. The CS algorithm illustrated in FIG. 8 follows certain of the preliminary steps of the NND and WNC algorithms in plotting the 2-D data points. A simplified and more efficient CS algorithm is illustrated in FIG. 10 and is described below.

Steps S802–S812 of FIG. 8 are performed in the manner described above for steps S402–S412, except that the bin size is 24 ms×24 ms in this algorithm. The abscissa and ordinate axes range from −600 ms to +600 ms, and forty bins are defined along these axes. This bin size and number of bins was found to be best after rigorous optimization. The bins shown in FIG. 9 are for illustrative purposes only and may not match the specifications described above. In step S814, the counts of the 2-D data points that fall into all of the bins is accumulated. Then, the MaxVal is determined in step S816, the nZeroCntnZeroCnt is determined in step S818, and the loCnt is determined in step S820. The counts of steps S814–S820 can be completed upon the time-out of the two-minute window as indicated in step S806, or the counts can be incremented each time a new ΔRR interval is determined in step S810 or stored in step S812 during a two-minute interval. A composite CS metric (CSM=loCnt+nZeroCnt−MaxVal) is then computed in step S822. The loCnt and nZeroCntcan each by themselves act as an AF discrimination metric to detect AF episodes, and the MaxVal can act as an AFL discrimination metric to detect pure AFL. The composite CS metric can be used to detect AF and pure AFL episodes simultaneously by comparison of the CS metric CSM to the thresholds for AF and AFL in steps S824 and S826.

A larger number of bins has at least one 2-D data point when the 2-D data points of the Lorenz plot are sparse and more uniform in distribution (a more uniform formation) as in the case of AF as shown in FIG. 1A. Thus, the nZeroVal count is relatively large compared to the nZeroVal count that is derived from a clustered distribution characteristic of NSR shown in FIG. 1B or with or without PVC/PAC shown in FIG. 1D or AFL shown in FIG. 1C.

In addition, a larger number of bins will be have between 1 and N (e.g., N=6) 2-D data points when the 2-D data points of the Lorenz plot are sparse and more uniform in distribution (a more uniform formation) as in the case of AF as shown in FIG. 1A. So for an AF segment, the loCnt metric is also relatively high compared to the loCnt metric that is derived in a clustered distribution of 2-D data points characteristic of NSR with or without PVC/PAC as shown in FIGS. 1B and 1D or AFL as shown in FIG. 1C.

Conversely, the MaxVal metric is higher for a clustered distribution than a MaxVal metric derived from a more uniform distribution or formation because there is higher probability that one bin will be filled with a higher number of 2-D data points. The MaxVal metric is useful for detecting tight atrial flutters because it has a very large value that is significantly larger than a MaxVal metric derived from Lorenz plots of segments exhibiting NSR with or without PVC/PAC ectopic beats. The MaxVal metric derived from Lorenz plots of segments exhibiting AF will have a very low value close to zero.

Therefore, these sub-metrics of the CS algorithm of FIG. 8 can be used together to calculate the CS metric CSM in step S822. The CS metric CSM is a relatively large positive number in the case of a two-minute segment exhibiting AF and relatively low negative number in the case of a two-minute segment exhibiting AFL. Therefore, the CS metric CSM is relatively robust in distinguishing AF from AFL, and both AF and AFL from NSR with or without PVC/PAC ectopic beats in steps S824–S830.

The $CSM_{AF\ SIG.\ METRIC}$ signature metric for AF and the $CSM_{AFL\ SIG.\ METRIC}$ signature metric for AFL can be derived a priori from confirmed episodes of AF and AFL in patient data specific to the patient and stored in memory of the IMD to be employed in the CSM algorithm. Confirmed episodes of AF can be processed through steps S802–S862 of FIG. 8 to derive the $CSM_{AF\ SIG.\ METRIC}$ signature metric, and confirmed episodes of AFL can be processed through steps S802–S862 of FIG. 8 to derive the $CSM_{AFL\ SIG.\ METRIC}$ signature metric. Further data of different segment length, as defined by the timer in step S806, may be used to detect the AF and AFL episodes separately. The two minute timer was found to be optimal for AF episodes, however smaller duration may be required to detect small tightly clustered AFL episodes.

The CSM can be derived in a simplified manner as each ΔRR interval is derived by determining the bin that the new 2-D data point falls into, and immediately incrementing the nZeroCnt and the MaxVal as appropriate, rather than plotting and otherwise storing the 2-D data points. In this variation of the CSM algorithm, there is no need to determine just which bin holds a 2-D data point. Instead, the nZeroCnt and the MaxVal are updated upon each ΔRR calculation. Furthermore, the loCnt can either be determined and employed or not employed in order to minimize memory use, energy consumption and computation steps and to enhance computation speed.

An alternative flow chart for the derivation of the CSM and determination of whether it satisfies the AF signature metric or the AFL signature metric is shown in FIG. 10. In step S1002, MaxVal is set to "1". nZeroVal is set to "0", and the two minute timer is started. Each time an R-wave is detected in step S1004, the ΔRR (dRR in the drawings) interval is calculated in step S1006, the 2D Lorenz plot of consecutive ΔRR interval is arithmetically indexed to a 1D memory structure of bins in steps S1008 and S1010, and the content of the indexed bin is incremented in step S1012. If the bin content is not greater than "1", then the nZeroCnt is incremented in step S1016. If the bin content exceeds "1", then the bin content is compared to the current maxVal in step S1018. The maxVal is set to the bin content in step S1020 if the current bin content exceeds the current maxVal. Initially the maxVal is set to "1", and so the maxVal is incremented to "2" as soon as any bin content=2, and then the maxVal continues to be incremented each time the bin content of any single bin increases to be greater than the then current maxVal. This process of incrementing the nZeroCnt and the maxVal continues until the two minutes are timed out as determined in step S1022.

In step S1026, CSM is calculated by CSM=nZeroCnt−MaxVal. The loCnt is not calculated nor is it employed since it was found that the algorithm is sufficiently accurate and robust without it. The comparison of the CSM determined in step S1026 with the $CSM_{AF\ SIG.\ METRIC}$ signature metric for AF and the $CSM_{AFL\ SIG.\ METRIC}$ signature metric for AFL in step S1028 operates as described above with respect to steps S1024–S1030 of FIG. 8.

It should be noted that step S1026 can be bypassed as shown in FIG. 10, and the nZeroCnt can itself be compared to the $CSM_{AF\ SIG.\ METRIC}$ in step S824 to determine if it is satisfied by the nZeroCnt. Similarly, the MaxVal can itself be compared to the $CSM_{AFL\ SIG.\ METRIC}$ to determine if it is satisfied by the MaxVal.

The $CSM_{AF\ SIG.\ METRIC}$ signature metric for AF and the $CSM_{AFL\ SIG.\ METRIC}$ signature metric for AFL can be derived a priori from confirmed episodes of AF and AFL in patient data specific to the patient and stored in memory of the IMD to be employed in the CSM algorithm. Confirmed episodes of AF can be processed through steps S1002–S1026 of FIG. 10 to derive the $CSM_{AF\ SIG.\ METRIC}$ signature metric, and confirmed episodes of AFL can be processed through steps S1002–S1026 of FIG. 8 to derive the $CSM_{AFL\ SIG.\ METRIC}$ signature metric.

For each of the metrics for declaring AF, the NND WNC and CSM metrics, an additional sudden onset criterion may be used to further discriminate between AF and sinus tachycardia. Both AF and highly irregular sinus tachycardia episodes will have relative higher values for all the above metrics compared to NSR and will satisfy the greater than threshold criterion in step S1104 in FIG. 11. The distinction in that case is that AF episodes are sudden onset, i.e. the value of the metric changes suddenly. The sudden onset criterion looks for a sudden change in the metric value between the present two minute interval and the median of last 3 two minute intervals in step S1110. If this difference is greater than the sudden onset threshold in step S1112 then the AF state is TRUE (AF is declared) in step S1114. If the metric satisfies the AF threshold in step S1104 and the sudden onset criterion is not met in step S1112 then the episode is declared as sinus tachycardia in step S1116. Once the sudden onset criterion is met the NND metric has to satisfy the AF threshold for subsequent intervals to maintain the AF state as TRUE and this achieved by steps S1106, S1118, S1120. If the metric value falls below the AF offset threshold in step S1104 and stays that way for a number of 2 minute segments, defined by AF $END_{BLOCKS}$ in step S1124, then the AF state is declared FALSE in step S1128.

If the sudden onset criterion is elected to be part of the detection procedure then the steps S1102–S1128 shown in FIG. 11 should replace the AF detection steps S432–434, S628–630, S824–826, S1026 in FIGS. 4, 6, 8, 10 respectively.

The scope of the algorithms may be extended by considering Lorenz plots of multiple dimensions. Lorenz plots shown in FIGS. 1, 5, 7, 9 are 2D plots. These plots can be extended to multiple dimensions by considering more number of ΔRR points. For example a 3D Lorenz plot can be obtained by plotting three successive ΔRR values along three different axes to obtain one point in the 3D plot. Further, the rules for forming the bins can be made non-linear with different bins having different sizes. Also the bins at the extreme edges of the plot may include data points which are beyond the value for that bin to accommodate for an infinite extent of ΔRR values.

The above-described algorithms work on segments of ΔRR lengths (i.e., the difference between successive cycle lengths). The declarations of AF or AFL or the absences of same is provided after a set segment has been processed, such as a two-minute segment of beats or a segment with a set number of beats. Part of each algorithm can be completed on a per-beat basis, and for a final calculation is performed after all the data for that segment is processed. The algorithms assume an unbroken stream of ventricular heartbeats, and the algorithms would need a flag to identify any gaps (lost beats or segments of beats). Other tachyarrhythmia event detection criteria can be integrated with these detection algorithms, such as high rate and sudden onset detection. The activity level of the patient can also be correlated with heart rate.

The algorithms of the present invention are all at least reasonably robust with respect to noise. However, it is useful to identify a long segment of noisy heartbeats and not process such noisy segments as described for example in commonly assigned U.S. Pat. No. 6,230,059. Since the algorithms analyze the statistical nature of the RR or ΔRR intervals, it is permissible to have RR or ΔRR data gaps comprising missing beats or segments of beats, but the algorithms need to know where those gaps occur.

The incoming heartbeats, e.g., a time segment of RR intervals, could be buffered examined for noise or gaps and only processed employing the above-described algorithms when the relatively short buffered segment of heartbeats is declared to not be a segment of noisy beats or having gaps. Each segment that is declared to be noisy or having gaps is discarded, and the process is repeated until buffer of beats has been collected that is not declared noisy or having gaps. There could be a counter of bad beat segments, such that if too many are discarded since the start of collecting the larger (i.e., two-minute segment) of data, that whole segment is reset and the process restarted. This is to prevent collecting data over such a long period of time that the body is not in the same physiological state at the end as at the beginning. As an initial recommendation, it is preferable not to let the time of collection of a data segment exceed twice the normal time. For example, it is better to reset the algorithm and provide a "don't know" as an algorithm output if a total of two-minutes of noisy segments are declared and discarded while collecting a single two-minute segment.

A second way is to discard and restart the processing of the algorithm if the desired segment time length is not reached before a noisy segment or condition is declared. The first way is more robust than the second, but is more complex.

It is anticipated that the processing of other diagnostic information is occurring, as needed, in parallel with the performance of the algorithms of the present invention. The diagnostic information needed varies with the specific clinical use of an IMD or EMD. For example, if a physician is using the algorithms in an IMD or EMD to assess rate control of a patient, two sets of histograms of ventricular rates or RR intervals or ΔRR are collected, one for detected NSR segments and another for detected AF/AFL, segments. A third set could be collected for symptomatic segments where data collection is activated by the patient. Such data collection could be turned ON or OFF depending on clinical need, in order to conserve processing power (i.e., battery life) and memory.

Typically such information is permanently stored in memory after the decision for that segment has been made. For example, the histogram could be collected for a two-minute segment of data, and that histogram could be added to the corresponding collective histogram when the final decision has been made as to NSR, AF or AFL.

The above-described algorithms of the present invention provide a metric at the end of processing of each two-minute segment of RR and ΔRR data and also declare whether or not the metric satisfies detection criteria for AF or AFL. The declarations could be true/false declarations or could be a fuzzy declarations (for example, a value from 0 to 1, where 1 represents a high confidence of AF/AFL and 0 represent a high confidence of NSR).

These "declarations" can either be used directly or can be processed through an evidence counter requiring, for example, that if 6 out of 8 segments have been declared as AF/AFL, the entire segment of segments will be declared AF/AFL. Such and evidence counter could use the fuzzy inputs instead of simple true/false inputs so that if the average of the last N segments (for example, 8 two-minute segments) is above a threshold, the segment is declared as AF/AFL. With either approach (declaration at the end of each segment, or at the end of each segment of segments), information is stored when the declaration has been reached. The information stored depends on the specific clinical use; if no clinical functions have been disabled, all of the information will be stored. The statistics that have been calculated for that segment will be incorporated into the overall statistics.

Two data collections with a total of 41 patients were used for testing of the algorithms of the present invention, namely, the MIT-NIH AF database with 25 non-chronic AF patients and an internal, proprietary database—of 16 patients. The latter database includes a broader range of patients and of arrhythmias than the MIT-NIH database, making it very useful for development and validation. Of the 16 proprietary patient data sets, eight data sets include episodes paroxysmal AF or AFL, and eight data sets include episodes of sinus tachycardia.

The raw RR interval data of each recording from each patient in each database was segmented into two-minute segments, starting at the beginning of the recording. The truth for each two-minute segment was determined. The RR interval data is then analyzed by the algorithms of the present invention starting from the beginning of the recording. No a priori information was used, i.e., the two-minute segments are not aligned with the beginning of previously identified AF/AFL episodes. Thus, the algorithms of the present invention were tested under conditions similar to how they would function in clinical practice wherein the algorithms would process contiguous segments of data that would be expected to contain a mix of normal sinus rhythms and arrhythmias.

The recordings for each patient were analyzed by each of the algorithms of present invention resulting in decisions reached for each analyzed two-minute segment. The decisions reached by each algorithm were compared to the truth for each such two-minute segment, and ROC curves, sensitivity curves, specificity curves, positive predictive value, and negative predictive value were calculated employing standard techniques.

This methodology was followed for three sets of data, the MIT-NIH database, the proprietary database and a combined database. Part of the value of this is to compare how robustly the algorithms perform as the patient collective changes. For part of the robustness evaluation, a threshold was chosen on one of these and tested on the other, providing a metric of how robust each algorithm is to changes across patient cohorts.

The algorithms of the present invention perform particularly well, achieving high sensitivity and specificity (98% for each) of AF detection. The three algorithms are also computationally efficient and suitable for hardware implementation, making them appropriate for use in IMDs as well as external medical devices. Robustness is an important consideration to differentiate between the different algorithms that perform well. The CS algorithm exhibits the best overall performance and is computationally more efficient than the other, is robust to changing patient cohorts, and has the additional advantage that no additional computation is required to determine if the CSM satisfies either of the AFL signature metric or the AF signature metric. The NND algorithm is more robust than the CS algorithm and the WNC algorithm, but is computationally less efficient than the CS algorithm.

The present invention improves the performance of relatively simple implantable monitors that have very limited signal filtration and memory capacity and that are implemented in digital logic circuitry. It can also be used in external monitors, including event recorders and, Holter monitoring systems, as well as in the Holter analysis software that is used to analyze a Holter recording. The present invention can also be implemented in more complex and sophisticated, micro-processor based implantable monitors and therapy delivery IMDs.

The algorithms of the present invention can also be incorporated into an ICD providing a anti-tachyarrhythmia therapies for ventricular tachyarrhythmias particularly to identify the nature of episodes of apparent ventricular tachyarrhythmias that do not fully satisfy any detection criteria that would trigger delivery of such anti-tachyarrhythmia therapies. In other words, the algorithms of the present invention can be employed to operate continually or when a ventricular rate threshold is exceeded to determine whether a given ICD patient is susceptible to AF or AFL episodes as well as the malignant ventricular tachyarrhythmias that justified implantation of the ICD.

The algorithms of the present invention can also be incorporated into a processor readable medium containing instructions to cause the processor to utilize ventricular signals to access atrial patterns for monitoring, diagnosis and prediction in the treatment of atrial arrhythmias.

All patents and publications referenced herein are hereby incorporated by reference in their entireties.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A method of detecting atrial arrhythmias, comprising one or more of atrial fibrillation (AF) and atrial flutter (AFL) within a segment of ventricular heartbeats signified by intervals between successive ventricular heartbeats that exhibit discriminatory signatures when plotted as data points in a scatter-plot comprising:

defining an AF signature metric for AF representative of the sparse distribution of data points during AF episodes and an AFL signature metric representative of the clustering distribution of data points during AFL episodes;

determining each interval between successive ventricular heartbeats;

plotting each succeeding interval as a data point in a scatter-plot;

developing a discriminatory metric signifying the degree of sparseness or clustering of the data points of the scatter-plot;

declaring AF if the discriminatory metric satisfies the AF signature metric representative of the distribution of data points during AF; and declaring AFL if the discriminatory metric satisfies the AFL signature metric representative of the distribution of data points during AFL.

2. The method of claim 1, wherein the scatter plot is replaced by a 3-D plot having a first interval on the X axis, a succeeding interval on the Y axis, and a net succeeding interval on the Z axis.

3. The method of claim 2, wherein the scatter plot is replaced by a multidimensional plot having multi-dimensional axis in successive orders thereof.

4. The method of claim 1, wherein the scatter-plot is a Lorenz plot having an origin, and the plotting step further comprises assigning an abscissa value and an ordinate value referenced to the origin of the Lorenz plot to each data point.

5. The method of claim 1, wherein the step of determining the interval comprises determining the change in interval between each succeeding ventricular heart beat from a preceding ventricular heartbeat.

6. The method of claim 4 or 5, wherein rather than using RR or ΔRR, the absolute value RR or the absolute value of ΔRR is used.

7. The method of claim 4 or 5, wherein rather than using RR or ΔRR, a non-linear function RR or a no-linear function of ΔRR is used, such as the log of the absolute value multiplied by the sign of the value.

8. The method of claim 5, wherein the step of determining the interval includes one interval axis and a change between intervals axis.

9. The method of claim 5, wherein the scatter-plot is a Lorenz plot having an origin, and the plotting step further comprises assigning an abscissa value and an ordinate value referenced to the origin of the Lorenz plot to each data point, whereby the data point is a two-dimensional (2-D) data point.

10. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

determining the nearest neighbor distance (NND) between each bin having a 2-D data point and the nearest bin having a 2-D data point;

processing the NND of each bin to derive an NND metric quantifying the degree of dispersion of 2-D data points among the bins;

the defining step comprises establishing an NND signature metric for AF; and the declaring step comprises declaring AF if the derived NND metric satisfies the NND signature metric for AF.

11. The method of claim 5, 9 or 10, wherein the step of determining the interval includes arranging input variables comprising one of and combinations thereof, of interval, change of interval, filtered interval including a running media filter, sensor input including systolic pressure for that beta, blood oxygen pulse, or volume signals, timing information, including A-V intervals, beat morphology parameters, including wavelet match, QRS width, or frequency content.

12. The method of claim 10, wherein correlating with the bin is performed in a non-uniform manner, permitting some bins to occupy more space than other bins.

13. The method of claim 10, wherein points falling outside a central bin area are assigned to the nearest.

14. The method of claim 10, wherein points falling outside a central bin area are discarded (not counted).

15. The method of claim 10, wherein points falling outside a central bin area are assigned to a separate, extra bin, which is counted separately from the other bins.

16. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

defining a local search window;

determining the nearest neighbor distance (NND) between each bin having a 2-D data point and the nearest bin having a 2-D data point and that is within the defined search window; for each 2-D data point in a bin, determining the distance from origin (DFO);

weighting the NND for each 2-D data point as a function of distance from origin (DFO); and summing the weighted NNDs of all 2-D data points to derive an NND metric quantifying the degree of dispersion of 2-D data points among the bins;

the step of defining an AF signature metric comprises establishing an NND signature metric for AF; and the declaring step comprises declaring AF if the derived NND metric satisfies the NND signature metric for AF.

17. The method of claim 16, wherein the weighting step further comprises:

defining a minimum DFO and a maximum DFO;

according a high weight to the NND for each 2-D data point having a DFO greater than the minimum DFO and less than the maximum DFO; and according a low weight to the NND for each 2-D data point having a DFO less than the minimum DFO and greater than the maximum DFO;

whereby the NND metric is high when the dispersion of 2-D data points among the bins is great signifying AF affecting the ventricular heartbeats.

18. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

determining the nearest neighbor distance (NND) between each bin having a 2-D data point and the nearest bin having a 2-D data point;

processing the NND of each bin to derive an NND metric quantifying the degree of clustering of 2-D data points within one or more adjacent bin;

the step of defining an AFL signature metric comprises establishing an NND signature metric for AFL; and the declaring step comprises declaring AFL if the derived NND metric satisfies the NND signature metric for AFL.

19. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

determining the nearest neighbor distance (NND) between each bin having a 2-D data point and the nearest bin having a 2-D data point and that is within a defined search window;

subtracting the determined NND from a maximum NND of the scatter-plot to provide an inverted NND (iNND);

for each 2-D data point in a bin, determining the distance from origin (DFO);

weighting the iNND for each 2-D data point as a function of distance from origin (DFO); and summing the weighted iNNDs of all 2-D data points to derive an iNND metric quantifying the degree of dispersion of 2-D data points among the bins;

the step of defining an AFL signature metric comprises establishing an AFL signature metric quantifying the degree of clustering of 2-D data points within one or more adjacent bin; and the declaring step comprises declaring AFL if the derived iNND discriminatory metric satisfies the AFL signature metric for AFL.

20. The method of claim 19, wherein the weighting step further comprises:

defining a minimum DFO and a maximum DFO;

according a low weight to the NND for each 2-D data point having a DFO greater than the minimum DFO and less than the maximum DFO; and according a high weight to the NND for each 2-D data point having a DFO less than the minimum DFO and greater than the maximum DFO;

whereby the NND metric is high when the 2-D data points are highly concentrated at a short DFO signifying AFL affecting the ventricular heartbeats.

21. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

for each bin containing at least one 2-D data point, counting the number of 2-D data points within adjacent bins that are within a defined local window surrounding the bin;

determining a Null Count related to the number of bins that are within the local window that do not contain a 2-D data point; and processing the Null Counts to derive an weighted null count (WNC) metric quantifying the degree of dispersion of 2-D data points among the bins;

the step of defining an AFL signature metric comprises establishing a WNC signature metric for AF; and the declaring step comprises declaring AF if the derived WNC metric satisfies the WNC signature metric for AF.

22. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

for each bin containing at least one 2-D data point, counting the number of 2-D data points within adjacent bins that are within a defined local window surrounding the bin;

determining a Null Count related to the number of bins that are within the local window that do not contain a 2-D data point; and for each 2-D data point in a bin having a Null Count associated with it, determining the distance from origin (DFO);

weighting the Null Count for each 2-D data point as a function of distance from origin (DFO); and summing the Null Counts to derive an weighted null count (WNC) metric quantifying the degree of dispersion of 2-D data points among the bins;

the step of defining an AF signature metric comprises establishing a WNC signature metric for AF; and the declaring step comprises declaring AF if the derived WNC metric satisfies the WNC signature metric for AF.

23. The method of claim 22, wherein the weighting step further comprises:

defining a minimum DFO and a maximum DFO;

according a high weight to the Null Count for each 2-D data point having a DFO greater than the minimum DFO and less than the maximum DFO; and according a low weight to the Null Count for each 2-D data point having a DFO less than the minimum DFO and greater than the maximum DFO;

whereby the WNC metric is high when the dispersion of 2-D data points among the bins is great signifying AF affecting the ventricular heartbeats.

24. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

for each bin containing at least one 2-D data point, counting the number of 2-D data points within adjacent bins that are within a defined local window surrounding the bin as a Point Count;

processing the Point Counts to derive an weighted point count (WPC) metric quantifying the degree of clustering of 2-D data points among the bins;

the step of defining an AFL signature metric comprises establishing a WPC signature metric for AFL; and the declaring step comprises declaring AF if the derived WPC metric satisfies the WPC signature metric for AFL.

25. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

for each bin containing at least one 2-D data point, counting the number of 2-D data points within adjacent bins that are within a defined local window surrounding the bin to derive a Point Count;

for each 2-D data point in a bin having a Point Count associated with it, determining the distance from origin (DFO);

weighting the Point Count for each 2-D data point as a function of distance from origin (DFO); and summing the Point Counts to derive an weighted point count (WPC) metric quantifying the degree of clustering of 2-D data points among the bins;

the step of defining an AFL signature metric comprises establishing a WPC signature metric for AFL; and the declaring step comprises declaring AFL if the derived WPC metric satisfies the WPC signature metric for AFL.

26. The method of claim 25, wherein the weighting step further comprises:

defining a minimum DFO and a maximum DFO;

according a low weight to the Null Count for each 2-D data point having a DFO greater than the minimum DFO and less than the maximum DFO; and according a high weight to the Null Count for each 2-D data point having a DFO less than the minimum DFO and greater than the maximum DFO;

whereby the WNC metric is high when the 2-D data points are clustered within one or more bin signifying AFL affecting the ventricular heartbeats.

27. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

counting the number of 2-D data points added to each bin over the segment;

determining the highest number of 2-D data points in a single bin as a MaxVal;

counting the number of bins containing at least one 2-D data point as a nZeroCntnZeroCnt;

counting the number of bins containing at least one 2-D data point and a predetermined number of 2-D data points as a loCnt; and calculating the cluster signature metric (CSM) by:

$$CSM = loCnt + nZeroCnt - \text{MaxVal},$$

the step of defining an AF signature metric comprises establishing a CSM signature metric for AF; and the declaring step comprises declaring AF if the derived CSM satisfies the CSM signature metric for AF.

28. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

counting the number of 2-D data points added to each bin over the segment;

determining the highest number of 2-D data points in a single bin as a MaxVal;

counting the number of bins containing at least one 2-D data point as a nZeroCnt;

counting the number of bins containing at least one 2-D data point and a predetermined number of 2-D data points as a loCnt; and calculating the cluster signature metric (CSM) by:

$$CSM = loCnt + nZeroCnt - \text{MaxVal},$$

the step of defining an AFL signature metric comprises establishing a CSM signature metric for AFL; and the declaring step comprises declaring AFL if the derived CSM satisfies the CSM signature metric for AFL.

29. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

counting the number of 2-D data points added to each bin over the segment;

determining the highest number of 2-D data points in a single bin as a MaxVal;

counting the number of bins containing at least one 2-D data point as a nZeroCnt;

counting the number of bins containing at least one 2-D data point and a predetermined number of 2-D data points as a loCnt; and calculating the cluster signature metric (CSM) by:

$$CSM = loCnt + nZeroCnt - \text{MaxVal},$$

the step of defining an AF signature metric comprises establishing a CSM signature metric for AF;

the step of defining an AF signature metric comprises establishing a CSM signature metric for AF; and the declaring step comprises declaring AF if the derived CSM satisfies the CSM signature metric for AF and declaring AFL if the derived CSM satisfies the CSM signature metric for AFL.

30. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

incrementing a count of the number of bins containing at least one 2-D data point as a nZeroCnt upon each occurrence of a 2-D data count;

determining the maximum number of 2-D data points accumulated in any bin over the segment as a MaxVal; and calculating the cluster signature metric (CSM) by:

$$CSM = nZeroCnt - \text{MaxVal},$$

the step of defining an AF signature metric comprises establishing a CSM signature metric for AF; and the declaring step comprises declaring AF if the derived CSM satisfies the CSM signature metric for AF.

31. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

incrementing a count of the number of bins containing at least one 2-D data point as a nZeroCnt upon each occurrence of a 2-D data count;

determining the maximum number of 2-D data points accumulated in any bin over the segment as a MaxVal; and calculating the cluster signature metric (CSM) by:

$$CSM = nZeroCnt - MaxVal,$$

the step of defining an AFL signature metric comprises establishing a CSM signature metric for AFL; and the declaring step comprises declaring AFL if the derived CSM satisfies the CSM signature metric for AFL.

32. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

incrementing a count of the number of bins containing at least one 2-D data point as a nZeroCnt upon each occurrence of a 2-D data count;

determining the maximum number of 2-D data points accumulated in any bin over the segment as a MaxVal; and calculating the cluster signature metric (CSM) by:

$$CSM = nZeroCnt - MaxVal,$$

the step of defining an AF signature metric comprises establishing a CSM signature metric for AF;

the step of defining an AFL signature metric comprises establishing a CSM signature metric for AFL; and the declaring step comprises declaring AF if the derived CSM satisfies the CSM signature metric for AF and declaring AFL if the derived CSM satisfies the CSM signature metric for AFL.

33. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises incrementing a count of the number of bins containing at least one 2-D data point as a nZeroCnt upon each occurrence of a 2-D data count;

the step of defining an AFL signature metric comprises establishing a CSM signature metric for AFL; and the declaring step comprises declaring AFL if the derived nZeroCnt satisfies the CSM signature metric for AFL.

34. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises determining the maximum number of 2-D data points accumulated in any bin over the segment as a MaxVal;

the step of defining an AFL signature metric comprises establishing a CSM signature metric for AFL; and the declaring step comprises declaring AFL if the derived MaxVal satisfies the CSM signature metric for AFL.

35. The method of claim 9, further comprising the steps of defining 2-D bins of the Lorenz plot with reference to the origin of the Lorenz plot and correlating each 2-D data point of the Lorenz plot with a bin of the Lorenz plot that the 2-D data point falls within and wherein:

the step of developing a discriminatory metric further comprises:

incrementing a count of the number of bins containing at least one 2-D data point as a nZeroCnt upon each occurrence of a 2-D data count; and determining the maximum number of 2-D data points accumulated in any bin over the segment as a MaxVal;

the step of defining an AF signature metric comprises establishing a CSM signature metric for AF;

the step of defining an AFL signature metric comprises establishing a CSM signature metric for AFL;

the declaring step comprises declaring AF if the derived nZeroCnt satisfies the CSM signature metric for AF and declaring AFL if the derived MaxVal satisfies the CSM signature metric for AFL.

36. Apparatus for detecting atrial arrhythmias, comprising one or more of atrial fibrillation (AF) and atrial flutter (AFL) within a segment of ventricular heartbeats signified by intervals between successive ventricular heartbeats that exhibit discriminatory signatures when plotted as data points in a scatter-plot comprising:

means for defining an AF signature metric for AF representative of the sparse distribution of data points during AF episodes and an AFL signature metric representative of the clustering distribution of data points during AFL episodes;

means for determining each interval between successive ventricular heartbeats;

means for plotting each succeeding interval as a data point in a scatter-plot;

means for developing a discriminatory metric signifying the degree of sparseness or clustering of the data points of the scatter-plot;

means for declaring AF if the discriminatory metric satisfies the AF signature metric representative of the distribution of data points during AF; and means for declaring AFL if the discriminatory metric satisfies the AFL signature metric representative of the distribution of data points during AFL.

37. The apparatus of claim 36, wherein the scatter-plot is a Lorenz plot having an origin, and the plotting step further comprises assigning an abscissa value and an ordinate value referenced to the origin of the Lorenz plot to each data point.

38. The method of claim 36, wherein the step of determining the interval comprises determining the change in interval between each succeeding ventricular heart beat from a preceding ventricular heartbeat.

39. A processor readable medium containing instructions to cause the processor to utilize ventricular signals to access atrial patterns for monitoring, diagnosis and prediction in the treatment of atrial arrhythmias comprising:

determining each interval between successive ventricular heartbeats comprising;

plotting each succeeding interval as a data point in a scatter-plot having an origin;

developing a metric signifying the degree of sparseness or clustering of the data points within the scatter-plot and with respect to the origin;

defining one or more of a sparseness discriminatory signature of data points in the scatter-plot representative of the distribution of data points with respect to origin during AF and a clustering discriminatory signature of data points in the scatter-plot representative of the distribution of data points with respect to origin during AFL; and declaring one or more of AF or AFL if the metric exhibits the sparseness discriminatory signature representative of the distribution of data points during AF and of AFL if the metric exhibits the clustering discriminatory signature representative of the distribution of data points during AFL.

40. The medium of claim 39, wherein the scatter-plot is a Lorenz plot and the plotting step further comprises assigning an abscissa value and an ordinate value referenced to the origin of the Lorenz plot to each data point.

41. The medium of claim 40, wherein the step of determining the interval comprises determining the change in interval between each succeeding ventricular heart beat from a preceding ventricular heartbeat.

* * * * *

UNITED STATES PATENT AND TRADEMARK OFFICE
CERTIFICATE OF CORRECTION

| | |
|---|---|
| PATENT NO. | : 7,031,765 B2 |
| APPLICATION NO. | : 10/292285 |
| DATED | : April 18, 2006 |
| INVENTOR(S) | : David E. Ritscher et al. |

It is certified that error appears in the above-identified patent and that said Letters Patent is hereby corrected as shown below:

Col. 25, line 12, delete "and a net succeeding" and insert --and a next succeeding--.

Col. 25, line 15, delete "multidimensional" and insert --multi-dimensional--.

Signed and Sealed this

Twenty-sixth Day of December, 2006

JON W. DUDAS
*Director of the United States Patent and Trademark Office*